United States Patent
Brugger et al.

(10) Patent No.: US 6,554,789 B1
(45) Date of Patent: Apr. 29, 2003

(54) LAYERED FLUID CIRCUIT ASSEMBLIES AND METHODS FOR MAKING THEM

(75) Inventors: James M. Brugger, Newburyport, MA (US); Jeffrey H. Burbank, Boxford, MA (US); Dennis M. Treu, Bedford, NH (US); Robert Thomas, New Boston, NH (US)

(73) Assignee: NxStage Medical, Inc., Lawrence, MA (US)

( * ) Notice: Subject to any disclaimer, the term of this patent is extended or adjusted under 35 U.S.C. 154(b) by 0 days.

(21) Appl. No.: 09/513,902

(22) Filed: Feb. 25, 2000

Related U.S. Application Data

(60) Continuation-in-part of application No. 08/800,881, filed on Feb. 14, 1997, which is a division of application No. 09/451,238, filed on Nov. 29, 1999.

(51) Int. Cl.$^7$ .......................... A61M 37/00; C02F 1/44; B01D 35/00; B65D 37/00
(52) U.S. Cl. ..................... 604/6.11; 604/5.01; 210/646; 210/252; 222/207
(58) Field of Search ............................... 604/4.01, 6.01, 604/5.01–5.04, 6.09, 6.1, 6.11, 6.16, 403–416; 422/44; 210/645–47, 650–52, 739, 741, 744, 767, 790, 805, 85, 87–90, 97, 98, 252, 253, 256, 257.1–257.2, 258–262, 321.6, 321.71–321.72, 929, 416.1, 417–420, 194, 195.1–195.2; 383/32, 37; 222/129, 133–34, 206–207, 212–13, 544–45

(56) References Cited

U.S. PATENT DOCUMENTS

| | | |
|---|---|---|
| 3,709,222 A | 1/1973 | DeVries |
| 3,774,762 A | 11/1973 | Lichtenstein |
| 3,912,455 A | 10/1975 | Lichtenstein |
| 4,069,968 A | 1/1978 | Herman |

(List continued on next page.)

FOREIGN PATENT DOCUMENTS

| | | |
|---|---|---|
| FR | 2684879 | 6/1993 |
| WO | 98/30258 | 7/1998 |
| WO | 98/35710 | 8/1998 |
| WO | 98/52628 | 11/1998 |
| WO | 99/42150 | 8/1999 |
| WO | 00/02603 | 1/2000 |

OTHER PUBLICATIONS

Baldamus et al, Outcome of Long Term Hemofiltration, International Society of Nephrology, Dec. 28, 1994, pp. S–41–s46.

Quellhorst et al, Postdilution Hemofiltration is Rational and Preferable, Proc. Dialysis Transplant Forum, 1979 pp. 54–58.

Schaefer et al., Chronic Hemofiltration A Critical Evaluation of a New Method for the Treatment of Blood, Artificial Organs, vol. 2 No. 4, pp. 386–394.

(List continued on next page.)

Primary Examiner—Angela D. Sykes
Assistant Examiner—Patricia Bianco
(74) Attorney, Agent, or Firm—Proskauer Rose LLP

(57) ABSTRACT

A layered fluid circuit includes first and second panel sections formed from sealed sheets of flexible material. A pattern of seals is formed in the first panel section to define a first fluid circuit. A pattern of seals is formed in the second panel section to define a second fluid circuit. The flexible sheets are aligned to place the first and second panel sections in a relationship with the first fluid circuit overlaying the second fluid circuit. The layered fluid circuit can be placed in a tray for use. Defined operating regions can be formed in one or both fluid circuits, such as an in-line clamping regions, in-line pump tubes, or in-line sensor regions, or in-line fluid holding compartments, or combinations thereof.

41 Claims, 22 Drawing Sheets

U.S. PATENT DOCUMENTS

| | | |
|---|---|---|
| 4,127,481 A | 11/1978 | Malchesky et al. |
| 4,379,452 A | 4/1983 | DeVries |
| 4,468,329 A | 8/1984 | Shaldon et al. |
| 4,479,760 A | 10/1984 | Bilstad et al. |
| 4,479,761 A | 10/1984 | Bilstad et al. |
| 4,479,762 A * | 10/1984 | Bilstad et al. ............... 206/364 |
| 4,514,295 A | 4/1985 | Mathieu et al. |
| 4,526,515 A | 7/1985 | DeVries |
| 4,537,561 A | 8/1985 | Xanthopoulos |
| 4,610,781 A | 9/1986 | Bilstad et al. |
| 4,692,138 A | 9/1987 | Troutner et al. |
| 4,702,829 A | 10/1987 | Polaschegg et al. |
| 4,711,715 A | 12/1987 | Polaschegg |
| 4,713,171 A | 12/1987 | Polaschegg |
| 4,737,140 A | 4/1988 | Lee et al. |
| 4,892,518 A | 1/1990 | Cupp et al. |
| 4,894,150 A | 1/1990 | Schurek et al. |
| 4,923,598 A | 5/1990 | Schal |
| 4,997,570 A | 3/1991 | Polaschegg |
| 5,041,098 A | 8/1991 | Loiterman et al. |
| 5,125,891 A | 6/1992 | Hossain et al. |
| 5,204,681 A | 4/1993 | Greene |
| 5,211,849 A | 5/1993 | Kitaevich et al. |
| 5,230,702 A | 7/1993 | Lindsay et al. |
| 5,291,205 A | 3/1994 | Greene |
| 5,330,448 A | 7/1994 | Chu |
| 5,344,568 A | 9/1994 | Kitaevich et al. |
| 5,350,357 A | 9/1994 | Kamen et al. |
| 5,441,636 A | 8/1995 | Chevallet et al. |
| 5,462,416 A | 10/1995 | Dennehey et al. |
| 5,484,397 A | 1/1996 | Twardowski |
| 5,522,998 A | 6/1996 | Polaschegg |
| 5,536,412 A | 7/1996 | Ash |
| 5,581,257 A | 12/1996 | Greene et al. |
| 5,614,677 A | 3/1997 | Wamsiedler et al. |
| 5,616,305 A | 4/1997 | Mathieu |
| 5,730,713 A | 3/1998 | Okarma et al. |
| 5,762,805 A | 6/1998 | Truitt et al. |
| 5,776,345 A | 7/1998 | Truitt et al. |
| 5,799,690 A * | 9/1998 | Jacobsen et al. ........ 137/533.11 |
| 5,836,908 A | 11/1998 | Beden et al. |
| 5,846,419 A | 12/1998 | Nederlof |
| 5,858,238 A | 1/1999 | McRea et al. |
| 5,871,694 A * | 2/1999 | Beden et al. ................ 210/101 |
| 5,902,336 A | 5/1999 | Mishkin |
| 5,910,252 A | 6/1999 | Truitt et al. |
| 5,919,369 A | 7/1999 | Ash |
| 5,923,001 A | 7/1999 | Morris et al. |
| 5,944,709 A | 8/1999 | Barney et al. |
| 6,022,335 A | 2/2000 | Ramadan |

OTHER PUBLICATIONS

Quellhorst et al, Long–Term Morbidity: Hemofiltration vs. Hemodialysis Dialysis Membranes: Structure and Predictions Contrib Nephrol. Basel, Karger, 1995, vol. 13, pp 110–119.

Collins et al, Clinical Comparison of Hemodialysis and Hemofiltration, Kidney Int Suppl 1985 Dec.; 17: S18–22.

Manns et al, The acu–men: A new device for continuous renal replacement therapy in acute renal failure, Kidney International, vol. 54, 1998, pp 268–274.

Prisma System Operator's Manual Feb. 1997, Gambro Healthcare.

Diapact CRRT Operating Manual Version 2.2—Mar 1998, M. Braun Melsungen AG.

Weiss et al, four years' experience of long–term hemofiltration in a Swedish Center; Scand J Urol Nephrol 1989; 23(3):223–9.

\* cited by examiner

LAYERED FLUID CIRCUIT ASSEMBLIES AND METHODS FOR MAKING THEM

RELATED APPLICATIONS

This application is a continuation-in-part of co-pending U.S. patent application Ser. No. 08/800,881, filed Feb. 14, 1997, and entitled "Hemofiltration System," which is incorporated herein by reference. This application is also a divisional of co-pending U.S. patent application Ser. No. 09/451,238, filed Nov. 29, 1999, and entitled "Systems and Methods for Performing Frequent Hemofiltration," which is incorporated herein by reference.

FIELD OF THE INVENTION

This invention relates to systems and methods for processing blood, e.g., for filtration, pheresis, or other diagnostic or therapeutic purposes.

BACKGROUND OF THE INVENTION

There are many types of continuous and intermittent blood processing systems, each providing different therapeutic effects and demanding different processing criteria.

For example, hemofiltration emulates normal kidney activities for an individual whose renal function is impaired or lacking. During hemofiltration, blood from the individual is conveyed in an extracorporeal path along a semipermeable membrane, across which a pressure difference (called transmembrane pressure) exists. The pores of the membrane have a molecular weight cut-off that can thereby pass liquid and uremic toxins carried in blood. However, the membrane pores can not pass formed cellular blood elements and plasma proteins. These components are retained and returned to the individual with the toxin-depleted blood. Membranes indicated for hemofiltration are commercially available and can be acquired from, e.g., Asahi Medical Co. (Oita, Japan).

After hemofiltration, fresh physiologic fluid is supplied to toxin-depleted blood. This fluid, called replacement fluid, is buffered either with bicarbonate, lactate, or acetate. The replacement fluid restores, at least partially, a normal physiologic fluid and electrolytic balance to the blood. Usually, an ultrafiltration function is also performed during hemofiltration, by which liquid is replaced in an amount slightly less than that removed. Ultrafiltration decreases the overall fluid level of the individual, which typically increases, in the absence of ultrafiltration, due to normal fluid intake between treatment sessions.

Following hemofiltration, fluid balancing, and ultrafiltration, the blood is returned to the individual.

SUMMARY OF THE INVENTION

One aspect of the invention provides a layered fluid circuit. The circuit includes first and second panel sections formed from sealed sheets of flexible material. A pattern of seals is formed in the first panel section to define a first fluid circuit. A pattern of seals is formed in the second panel section to define a second fluid circuit. The flexible sheets are aligned to place the first and second panel sections in a relationship with the first fluid circuit overlaying the second fluid circuit.

According to another aspect of the invention, first and second sheets of flexible material are sealed to form the first and second panel sections. The flexible sheets are folded over to place the first and second panel sections in a reverse facing relationship, with the first fluid circuit overlaying the second fluid circuit.

In certain embodiments, at least one of the fluid circuits includes a defined operating region, such as an in-line clamping region that closes in response to an exterior force to occlude flow in the fluid circuit, or an in-line pump tube, or an in-line sensor region to transmit pressure to an exterior pressure sensor, or an in-line fluid holding compartment, or combinations thereof.

In one embodiment, both first and second fluid circuits include in-line clamping regions, which overlay each other. In this arrangement, the in-line clamping regions jointly close in response to an exterior force to occlude fluid flow in both the first and second fluid circuits.

In one embodiment, both the first and second fluid circuits include in-line fluid holding compartments, which overly each other. The overlaying compartments mutually form a two-compartment chamber.

In one embodiment, at least one length of flexible tubing extends from a panel section and is joined in fluid communication with one or both of the fluid circuits.

According to another aspect of the invention, the fluid circuits defined by the aligned or folded over sheets are carried within the confines of a tray.

In other embodiments, the tray includes one or more cut-out regions that expose operating regions of the fluid circuits, such as in-line clamping regions, or in-line pump tubes, or in-line sensor regions, or in-line fluid holding compartments, or combinations thereof.

Another aspect of the invention provides a fluid circuit for volumetrically balancing fluid. The fluid circuit comprises first and second sheets of flexible material sealed to form first and second panels. A pattern of seals formed in the first panel defines a first fluid circuit for handling out going fluid. The first fluid circuit includes a first in-line compartment to retain a volume of out going fluid. A pattern of seals formed in the second panel defines a second fluid circuit for handing in going fluid. The second fluid circuit includes a second in-line compartment to retain a volume of in going fluid. The flexible sheets are aligned to place the first and second panels in a relationship with the first in-line compartment overlaying the second in-line compartment to mutually form a two-compartment chamber. The two-compartment chamber displaces out going fluid from the first in-line compartment as in going fluid is conveyed into the second in-line compartment, and vice versa.

Another aspect of the invention provides a method for forming a layered fluid circuit. The method seals first and second sheets of flexible material to form first and second panel sections. The method forms a pattern of seals in the first panel section to define a first fluid circuit, and also forms a pattern of seals in the second panel section to define a second fluid circuit. The method aligns the flexible sheets to place the first and second panel sections in a relationship with the first fluid circuit overlaying the second fluid circuit.

In one embodiment, the aligned flexible sheets are placed into a tray for use.

Other features and advantages of the inventions are set forth in the following specification and attached drawings.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

The various aspects of the invention will be described in connection with providing hemofiltration. That is because the features and advantages that arise due to the invention are well suited to the performance of hemofiltration. Still, it should be appreciated that the various aspects of the invention can be applied to achieve other blood processing objectives as well, such as hemodialysis and hemopheresis.

I. System for Providing Frequent Hemofiltration

Figure 1:
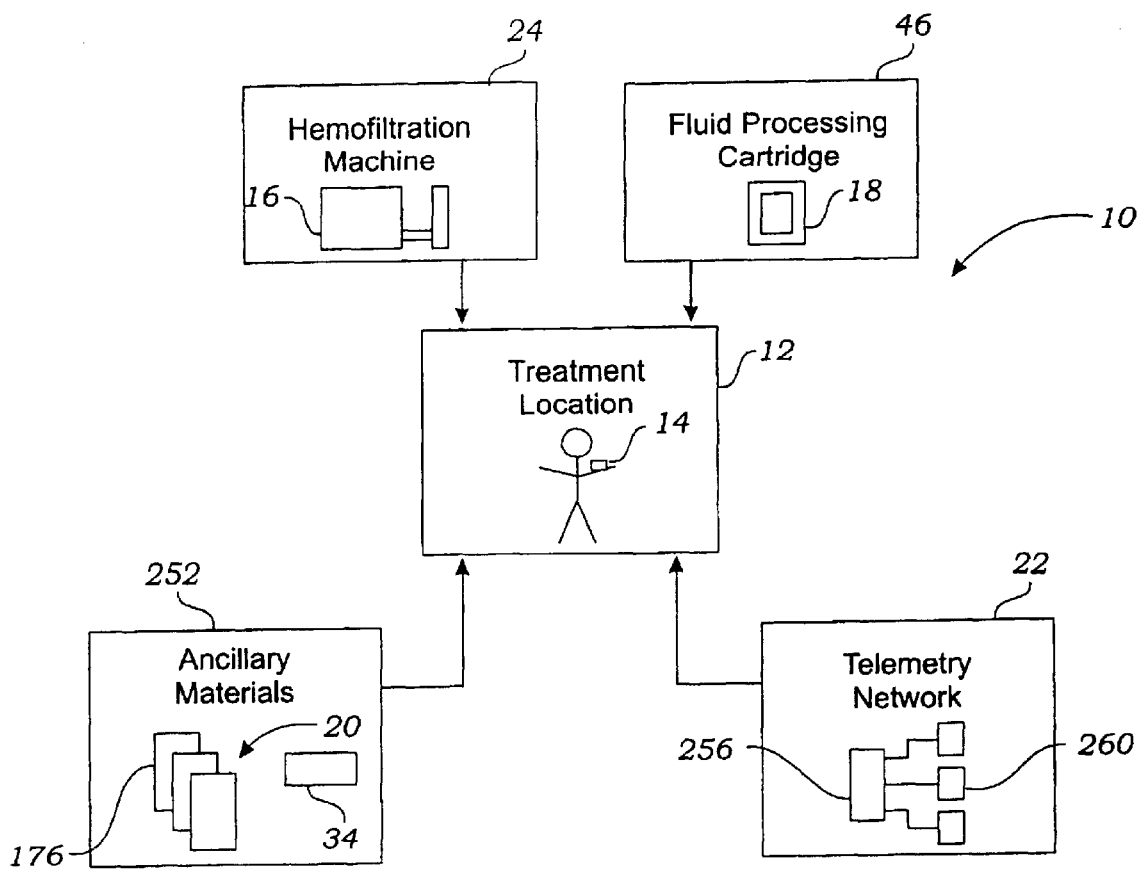
FIG. 1 is a diagrammatic view of a system that enables frequent hemofiltration by supplying to a treatment location a durable hemofiltration machine, a disposable fluid processing cartridge that fits on the machine, ancillary processing materials that the machine and cartridge use, and telemetry that supports the hemofiltration therapy.

FIG. 1 shows a system 10 that makes it possible for a person whose renal function is impaired or lacking, to receive convenient and therapeutically effective hemofiltration on a frequent basis, e.g., at least four times weekly and, preferably, six times weekly. The frequent hemofiltration therapy that the system 10 provides has as one of its objectives the maintenance of uremic toxin levels in the person's blood within a comfortable range, e.g., at no more than 80% of the maximum level. Through frequent hemofiltration, the system 10 can provide either acute or chronic treatment of renal impairment or failure.

The system 10 delivers the durable and disposable equipment and materials necessary to perform frequent hemofiltration on the person at a designated treatment location 12.

The location 12 can vary. It can, for example, be a setting where support and assistance by one or more medically trained care givers are immediately available to the person, such as at a hospital, an outpatient clinic, or another treatment center. Alternatively, the location 12 can comprise a setting where support or assistance are provided by a trained partner, such as in the person's residence.

By careful design of durable and disposable equipment, the system 10 can make it possible for the person to perform frequency hemofiltration in a non-clinical setting, without direct assistance from technically or medically trained persons.

To make frequent hemofiltration more convenient, the person preferably has been fitted with one or more vascular access devices 14. Each device 14, for example, may be generally constructed in the manner disclosed in pending U.S. patent application Ser. No. 08/724,948, filed Nov. 20, 1996, and entitled "Subcutaneously Implanted Cannula and Method for Arterial Access."

The devices 14 preferably support high blood flow rates at or above 300 ml/min and preferably at least 600 ml/min. The devices 14 also enable quick and frequent cannulation. The devices 14 thereby reduce the time required to set up, perform, and complete a frequent hemofiltration session. The high blood flow rates that the devices 14 support also increase the removal rate of uremic toxins during hemofiltration, as will be described in greater detail later.

To enable frequent hemofiltration, the system 10 supplies to the treatment location 12 a durable hemofiltration machine 16. The system 10 also supplies fluid processing cartridges 18 to the treatment location 12, for installation on the machine 16 at the time of treatment. The system 10 further supplies ancillary materials 20, such as replacement fluids, to the treatment location 12 for use in association with the cartridge 18 and machine 16. The system 10 also preferably supplies a telemetry network 22, to enable centralized, off-site monitoring and supervision of the frequent hemofiltration treatment regime.

The operation of the system 10 to provide these various functions will now be described in greater detail.

A. Supplying a Hemofiltration Machine

The system 10 includes a source 24 that supplies a hemofiltration machine 16 (which can also be called a "cycler") to the treatment location 12. The machine 16 is intended to be a durable item capable of long term, maintenance free use.

Figure 2:
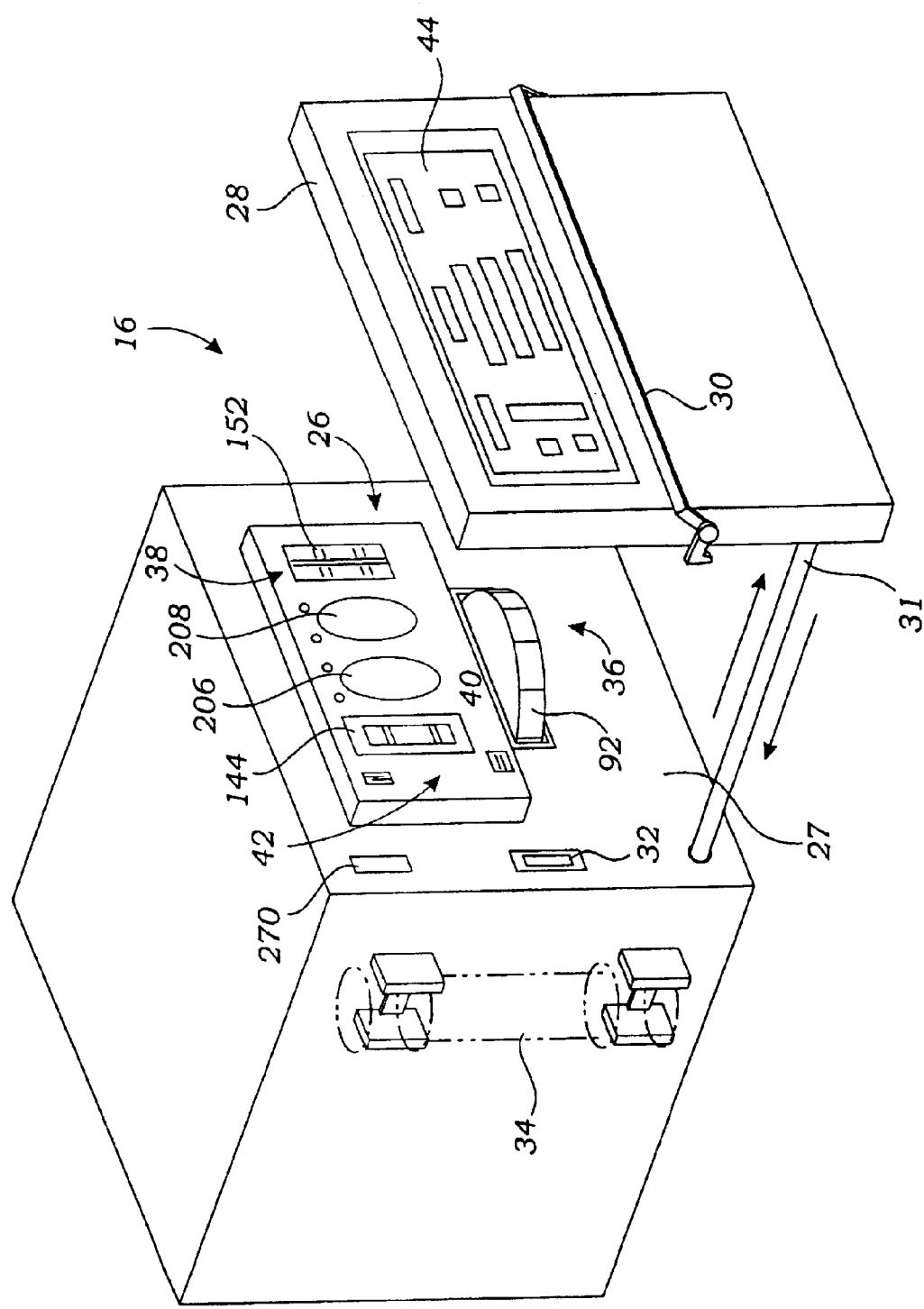
FIG. 2 is a front perspective view of a hemofiltration machine that the system shown in FIG. 1 supplies to a treatment location.

FIG. 2 shows a representative embodiment of a machine 16 capable of performing frequent hemofiltration. The machine 16 is preferably lightweight and portable, presenting a compact footprint, suited for operation on a table top or other relatively small surface normally found, e.g., in a hospital room or in a home. The compact size of the machine 16 also makes it well suited for shipment to a remote service depot for maintenance and repair.

Figure 3:
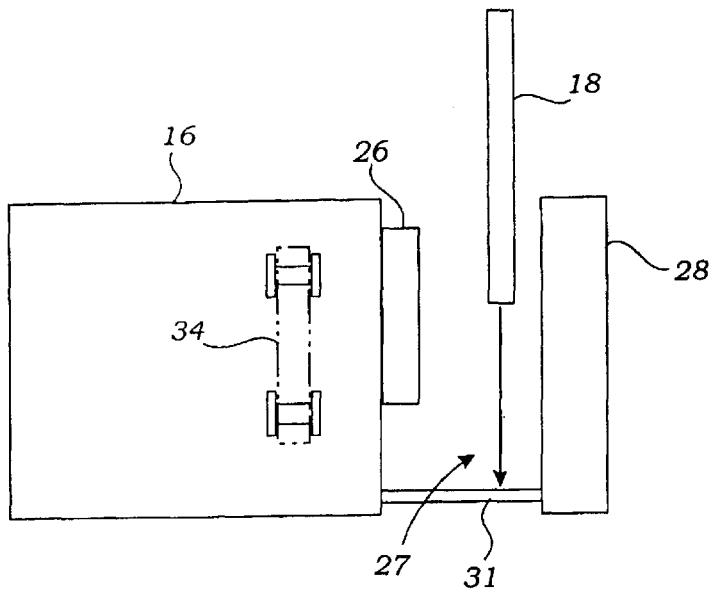
FIGS. 3 to 5 are side elevation views showing the loading into the machine shown in FIG. 2 of a fluid processing cartridge, which the system shown in FIG. 1 also supplies to the treatment location.
Figure 4:
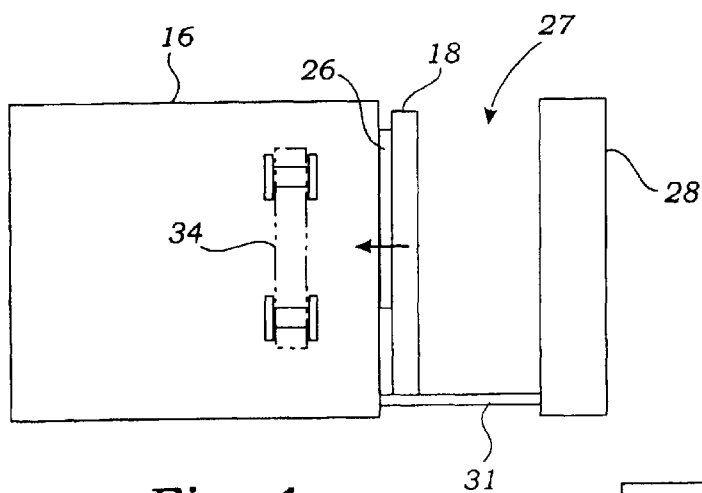
Figure 5:
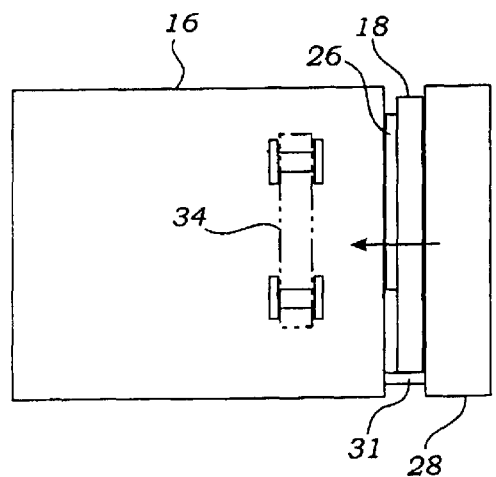

In the illustrated embodiment, the machine 16 includes a chassis panel 26 and a panel door 28 that moves on a pair of rails 31 in a path toward and away from the chassis panel 26 (as shown by arrows in FIG. 2). A slot 27 is formed between the chassis panel 26 and the door 28. As FIGS. 3 to 4 show, when the door 28 is positioned away from the panel 26, the operator can, in a simple vertical motion, move a fluid processing cartridge 18 into the slot 27 and, in a simple horizontal motion, fit the cartridge 18 onto a raised portion of the chassis panel 26. When properly oriented, the fluid processing cartridge 18 rest on the rails 31 to help position the cartridge 18. As FIG. 5 shows, movement of the door 28 toward the panel 26 engages and further supports the cartridge 18 for use on the panel 26 for use. This position of the door 28 will be called the closed position.

The machine 16 preferably includes a latching mechanism 30 and a sensor 32 (see FIG. 2) to secure the door 28 and cartridge against movement before enabling circulation of fluid through the cartridge 18.

As will be described in greater detail later, the processing cartridge 18 provides the blood and fluid interface for the machine 16.

The machine 16 pumps blood from the person, through the fluid processing cartridge 18 to a hemofilter 34 (mounted in brackets to the side of the chassis panel 26, as shown in phantom lines in FIGS. 2 to 5), back to the cartridge 18, and then back to the person.

Alternatively, the hemofilter 34 can form an integrated part of the cartridge 18. The hemofilter 34 is connected via the cartridge 18 to the person's blood supply through the vascular access devices 14.

The machine 16 includes a blood handling unit 36 mounted on the chassis panel 26. The blood handling unit 36 includes a peristaltic blood pump 92 and various clamping and sensing devices(described later). The blood handling unit 36 circulates the person's blood in a controlled fashion through the hemofilter 34 and back to the person. The hemofilter 34 removes waste fluid containing urea and other toxins.

The machine 16 also includes a fluid management unit 38 mounted on the chassis panel 26. The fluid management unit 38 includes a peristaltic waste and replacement fluid pump 152 and various clamping and sensing devices (described later). The fluid management unit 38 replaces the waste fluid with a sterile replacement fluid, for return with the treated blood to the person's blood supply. The replacement fluid also acts to maintain the person's electrolytic balance and acid/base balance.

The fluid management unit 38 includes a fluid balancing element 40 mounted on the chassis panel 26. The fluid balancing element 40 meters the return replacement fluid in proportion to the amount of waste fluid removed.

Figure 6A:
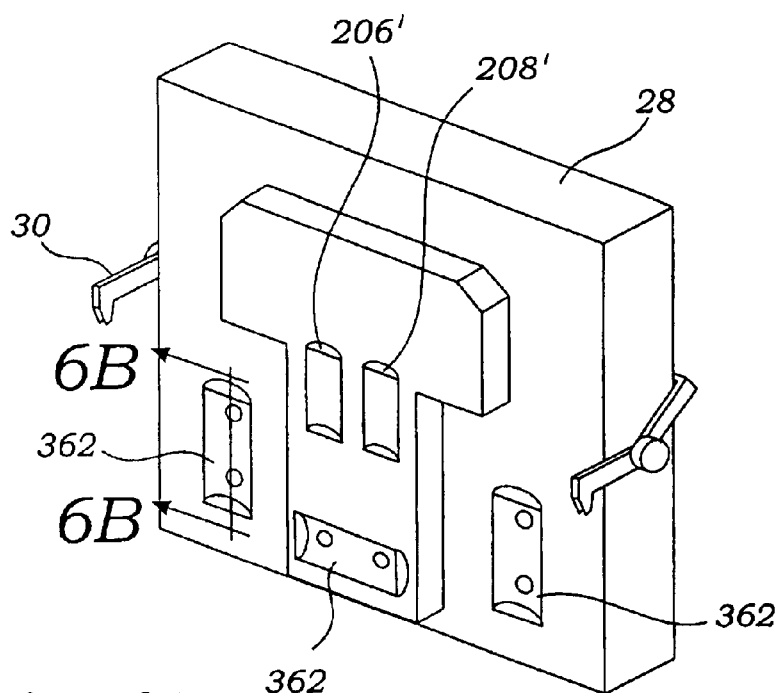
FIG. 6A is a perspective view of the inside of the door of the hemofiltration machine shown in FIG. 2.

In the illustrated embodiment, the fluid balancing element 40 includes one or more balancing chambers 206, 208 and associated clamping devices(the details of which will be described later). The chambers 206, 208 comprise preformed depressions formed in the raised portion of the chassis panel 26. As FIG. 6A shows, preformed depressions on the door 28 form mating chambers 206', 208', which register with the chassis panel chambers 206, 208. When the door 28 is closed, the registered chambers 206/206' and 208/208' define between them spaces of known volume, e.g., 20 ml. The known volume can, of course, be greater or less than 20 ml, and the chambers 206/206' and 208/208' can each have a different known volume.

As will be described in greater detail later, flexible containers 212 and 214, which form a part of a preformed fluid circuit carried within the fluid processing cartridge 18, fit into the registered chambers 206/206' and 208/208'. The chambers 206/206' and 208/208' and associated clamping devices interact with the containers 212 and 214, to provide the capability of balancing waste and replacement fluid volumetrically, in an accurate, straightforward manner, without use of weigh scales and weight sensing.

The machine 16 also includes an ultrafiltration unit 42 on the chassis panel 26. The ultrafiltration unit 42 includes a peristaltic ultrafiltration pump 144 to remove additional waste from the person without addition of replacement fluid. The machine 16 provides, at the end of each frequent hemofiltration session, a net ultrafiltration fluid loss, which coincides with an amount prescribed by the attending physician.

The machine 16 completes a frequent hemofiltration session when a prescribed replacement fluid volume has been exchanged and the net ultrafiltration fluid loss target has been met. The machine 16 can accommodate continuous or extended treatment sessions on an automated basis. The machine 16 can also accommodate operation based upon individually set ultrafiltration rates, blood flow rates, or return fluid flow rates, with completion determined by the volume of replacement fluid exchanged or by a treatment timer.

As will be described in greater detail later, the various pumping, clamping, and sensing devices on the machine 16 provide blood flow, fluid management, and safety functions by sensing pump pressures, detecting air, detecting blood leak through the hemofilter 34, and sensing waste pressure. The sensors also provide addition fluid management and safety functions, such as sensing replacement fluid temperature and replacement fluid pump pressure. The machine 16 also provides other processing functions, such as priming, supplying a replacement fluid bolus, and carrying out a rinseback of the person's blood.

The machine 16 also preferable includes an operator interface 44, which, in the illustrated embodiment (see FIG. 2) is carried on the exterior of the door 28. As will be described later, the interface 44 provides simple switch and/or knob operation of the machine 16, preferably by use of one hand. The interface 44 displays information necessary to operate the machine 16, presenting an uncluttered display and tactile touch buttons to intuitively lead a person without technical or medical background through set up and operation of the machine 16 with a minimum of training.

Further details of the machine 16, the pumps and sensing devices, and their interaction with the fluid processing cartridge 18 will be described later.

The source 24 supplying the machine 16 can comprise a company or business that manufactures the machine 16 or otherwise distributes the machine 16 to the treatment location 12 on a sale, lease, or rental basis.

B. Supplying a Fluid Processing Cartridge

The system 10 further includes a source 46 for supplying a fluid processing cartridge 18 to the treatment location 12 for use in association with the machine 16. The cartridge 18 is intended to be disposable item, capable of single or extended use, which the loads on the machine 16 before beginning a hemofiltration session (as FIGS. 3 to 5 show). The cartridge 18 can be removed from the machine 16 and discarded upon the completing the hemofiltration session, or its use can be extended to one or more subsequent sessions, as will be described later.

The cartridge 18 couples to the person's vascular access devices 14 and interacts with the machine 16 to draw, process, and return blood in a continuous, extracoporeal path, to carry out fluid balancing through waste removal, replacement fluid exchange, and ultrafiltration.

Preferably, the tasks of loading and unloading the cartridge 18 are simple and straightforward, following a simple, straight loading and unloading path into the slot 27 and against the chassis panel 26, as FIGS. 3 to 5 show. In this way, the person receiving hemofiltration can by himself/ herself set up the cartridge 18 and machine 16, without necessarily requiring assistance from a technically or medically trained person.

The cartridge 18 preferably provides the entire blood and fluid interface for the machine 16, including all pumping, valving, pressure sensing, air detection, blood leak detection, and tubing management. The cartridge 18 preferable is supplied to the treatment location 12 with all tubing, access needles and waste and replacement fluid connections preconnected. A waste bag also can be preattached, if desired, or the waste line can be placed in a drain.

Loading the cartridge 18 on the chassis panel 26 and closing the door 28 also automatically locates all sensors of the machine's safety function in association with the blood fluid interface. The operator is not required to load anything else to carry out the machine's safety function. Once the machine 18 undergoes start up testing to confirm cartridge placement and integrity and to confirm the functionality of the sensors, subsequent automated operation the machine 18 in a safe mode is assured.

Figure 7:
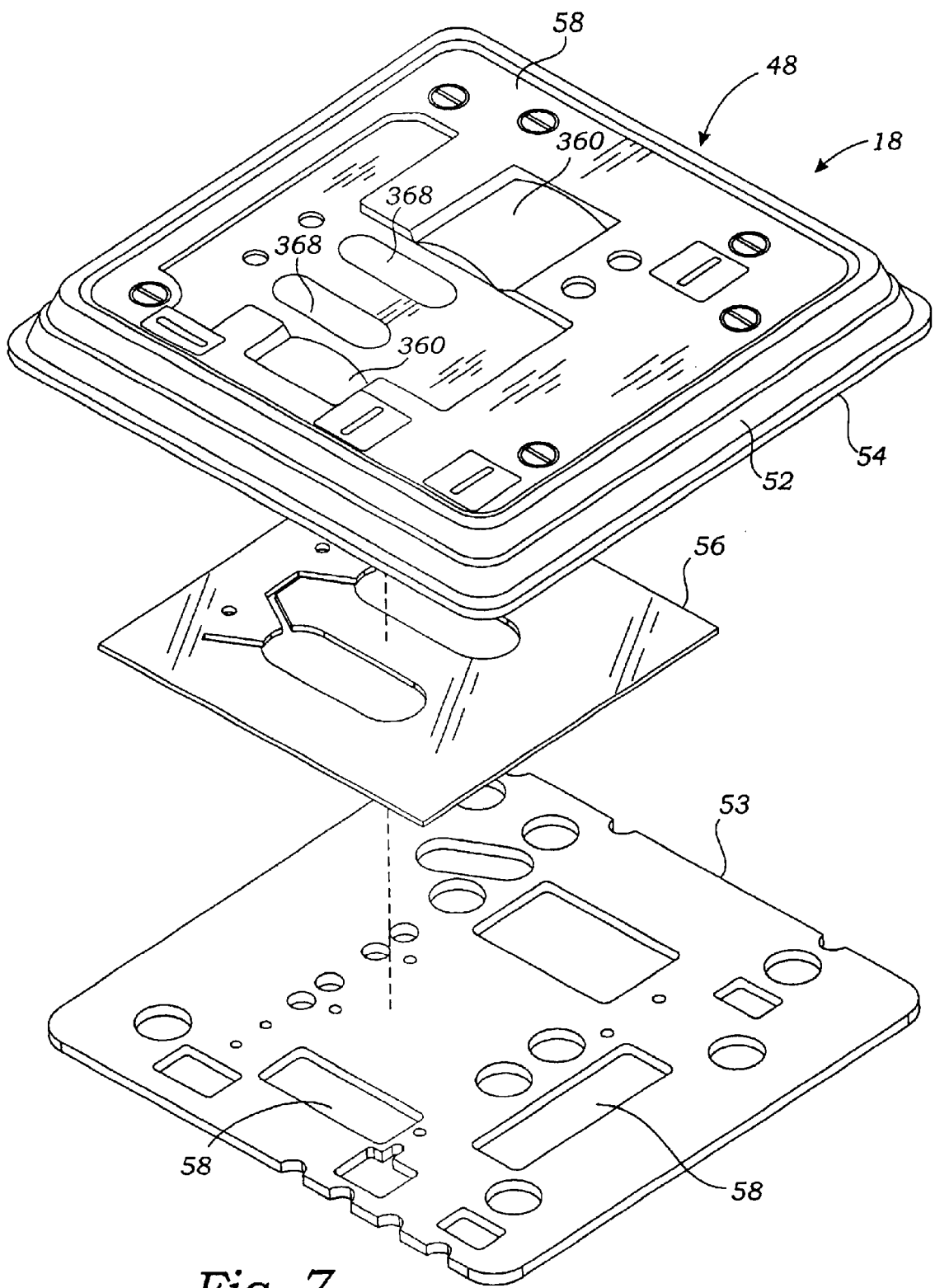
FIG. 7 is an exploded perspective view of one embodiment of the fluid processing cartridge that is supplied to the treatment location, comprising a tray in which a fluid processing circuit is contained.
Figure 8:
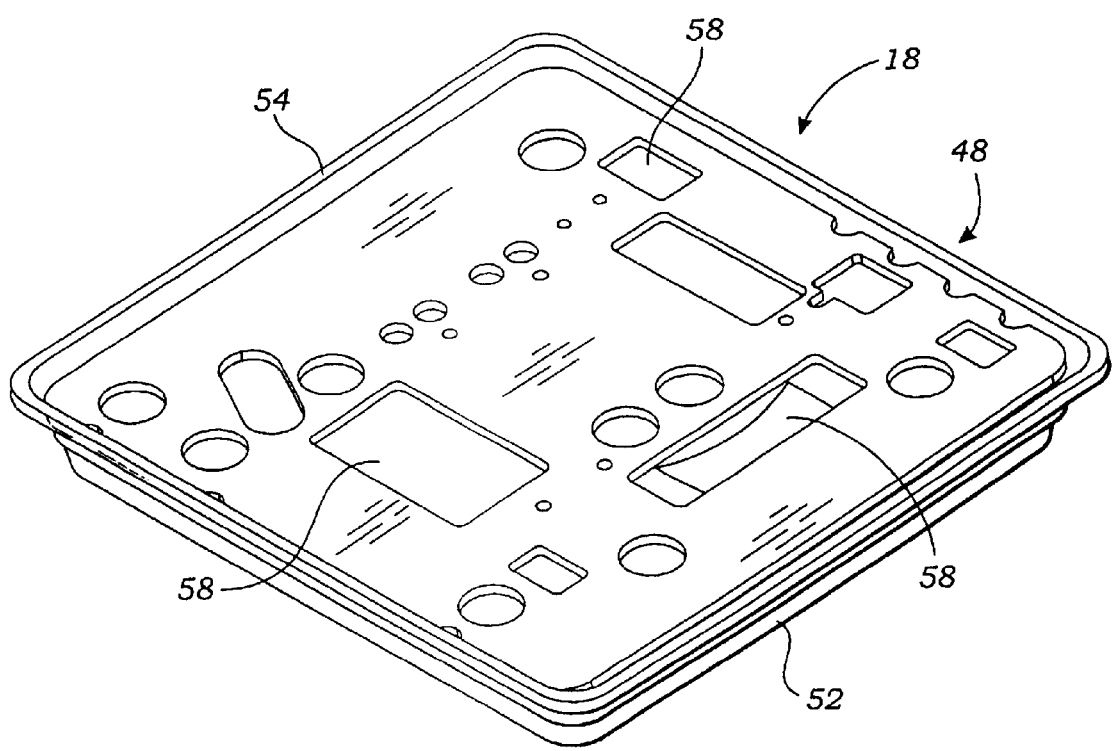
FIG. 8 is an assembled perspective view of the fluid processing cartridge shown in FIG. 7.

The cartridge 18 can be constructed in various ways. In the illustrated embodiment (see FIGS. 7 to 9), the cartridge 18 includes a preformed tray 48 and insert 53 manufactured, e.g., by thermoforming polystyrene or another comparable material. The tray 48 and insert 53 are peripherally joined together, e.g., by ultrasonic welding.

The tray includes a base 50, side walls 52, and an open top edge 54. The geometry of the tray 48 is appropriately keyed to fit in only one orientation on the rails 31 in the slot 27 between the chassis panel 26 and door 28 of the machine 16. When so fitted, the insert 53 rests on the raised portion of the chassis panel 26. Closing the door 28 secures the tray 48 to the panel 26.

A preformed circuit 56 is carried between the base 50 of the tray 48 and the insert 53 . The circuit 56 is arranged to carry blood, waste, and replacement fluid during hemofiltration.

As will be described in greater detail later, the circuit 56 includes an array of fluid flow paths formed with in-line flexible containers 212 and 214(for fluid balancing), peristaltic pump headers, sensor stations, tubing, and valve stations. The layout of flow paths, containers, pump headers, sensing stations, and valve stations on the circuit 56 form a mirror image of the layout of the structural and mechanical components on the chassis panel 26 and door 28 of the machine 16.

The insert 53 includes cut outs 58 to expose the containers, peristaltic pump headers, sensing stations, and valve stations for engagement with equipment on the chassis panel 26. When the tray 48 is fitted to the chassis panel 26, and the door 28 is closed, the in-line containers 212/214 formed in the circuit 56 fit within the registered chambers 206/206' and 208/208' on the chassis panel 26 and door 28. Likewise, the pump headers and the sensor and valve stations on the circuit 56 overlay and engage corresponding peristaltic pumps, sensors, and valve on the chassis panel 26.

Figure 6B:
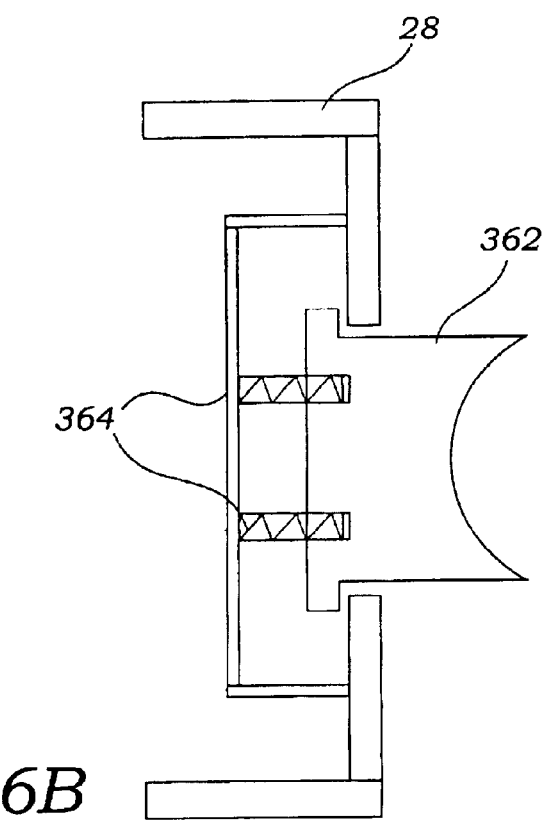
FIG. 6B is a side section view of a spring loaded pump race carried on the door shown in FIG. 6A, taken generally along line 6B—6B in FIG. 6A.

In the illustrated embodiment (see FIG. 7), the base 50 of the tray 48 underlaying the pump stations is relieved, to form pump races 360. The inside surface of the door 28 carries concave pump races 362 supported by springs 364 (see FIGS. 6A and 6B). When the door 28 is closed, the spring loaded pump races 362 on the door 28 nest with the relieved pump races 360 on the tray 48, to provide rigidity and support. Alternatively, the pump races 360 can form cutouts in the base 50 (like cut outs 58 in the insert, as earlier described), through which the pump races 362 on the door 28 extend.

The base 50 of the tray 48 underlying the containers 212/214 is also relieved, to form chamber supports 368. When the the door 28 is closed, the tray supports 368 fit within the door chambers 206' and 208'. The door 28 therefore engages the tray 48, to add overall rigidity and support to the tray base 50.

When the door 28 is closed, the containers 212/214 are enclosed within the registered chambers 206/206' and 208/ 208' and tray chamber supports 368, which define for the containers 212/214 to a known maximum volume. The peristaltic pumps, sensors, and valve stations on the machine 16 interact with the flexible components of the circuit 56.

The cartridge 18 makes possible direct, centralized connection of a blood-fluid interface to the blood pump, the waste and replacement pump, the ultrafiltration pump, the fluid balancing chambers, the sensor devices, and the clamping devices of the machine 16, with no air interfaces. The compact arrangement of the cartridge 18 also reduces fluid pressure drops, thereby accommodating high flow rates, e.g., an arterial blood line pressure drop of less than 250 mmHg at a flow rate of 600 ml/min and a hematocrit of 25.

Figure 9:
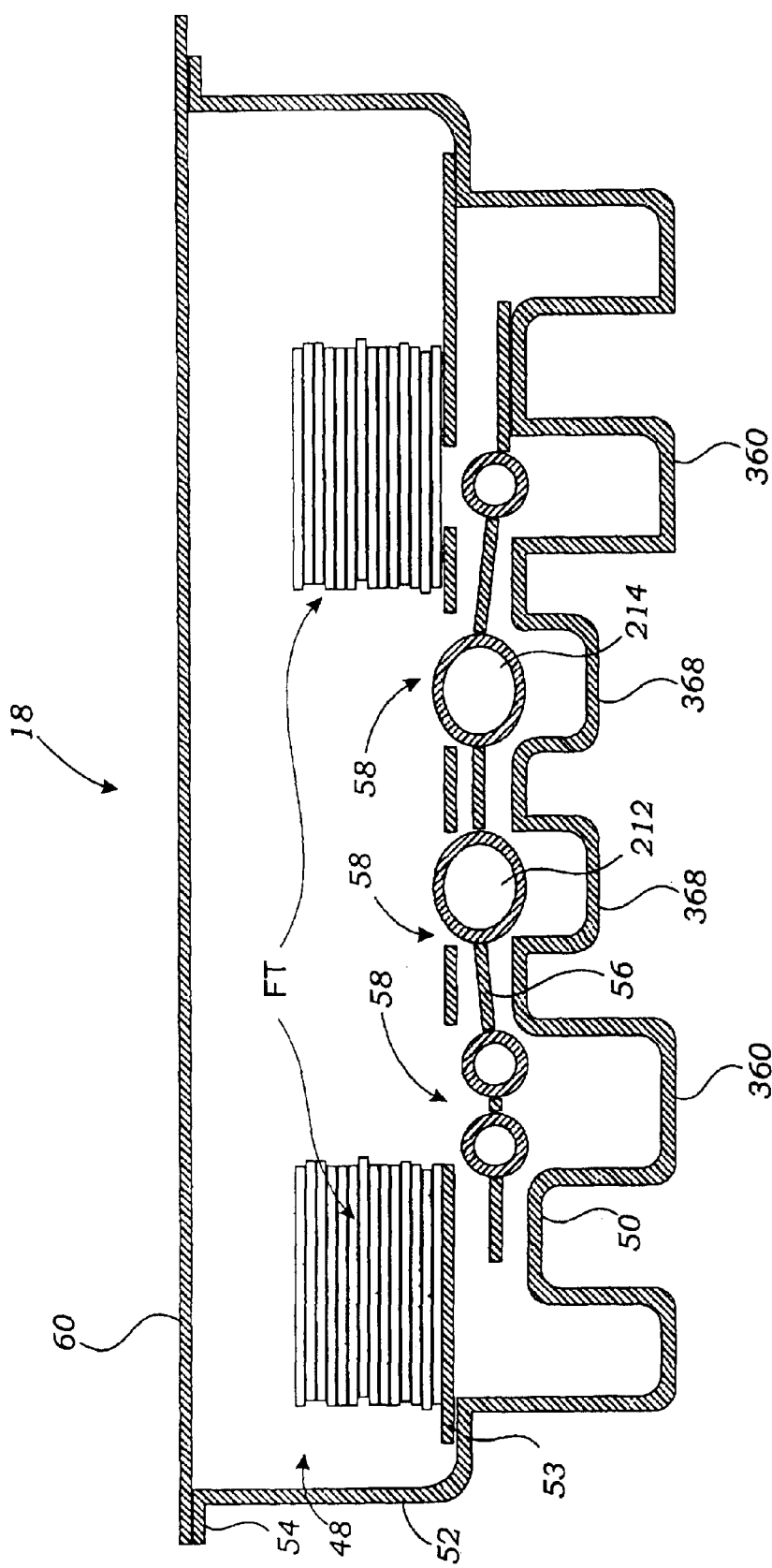
FIG. 9 is a side section view of the fluid processing cartridge shown in FIGS. 7 and 8, showing the cartridge as it is supplied in a closed, sterile condition to the treatment location.
Figure 10:
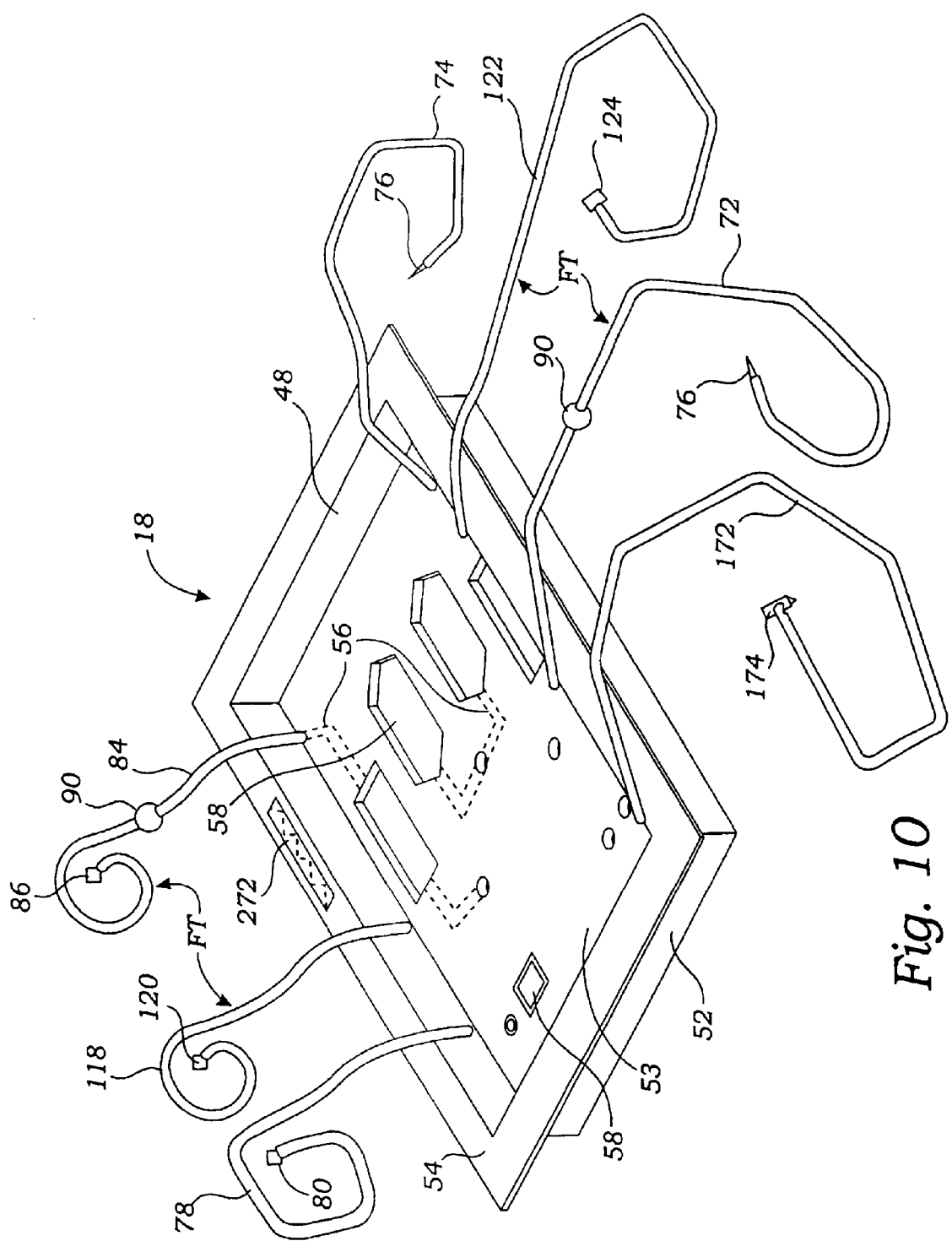
FIG. 10 is a perspective view of the cartridge shown in FIGS. 7 to 9, in preparation of being mounted on the hemofiltration machine shown in FIG. 2.

As FIGS. 9 and 10 show, lengths of flexible tubing FT are coupled to the circuit 56 in the base 50 of the tray 48 and rest in coils on top of the insert 53 within the tray 48 during shipment and before use (see FIG. 9). As FIG. 9 also shows, a removable lid 60, made, e.g., from ethylene oxide permeable TYVEKJ material or polyethylene plastic sheet stock, covers and seals the interior of the tray 48 prior to use. The cartridge 18 can therefore be sterilized by exposure to ethylene oxide prior to use. Other methods of sterilization, e.g., gamma radiation or steam sterilization, can be used. Alternatively, the ultrasonically welded assembly of the tray 58, insert 53, and the circuit 56 (with attached tubing FT) can be packaged as a unit into a sealed plastic bag for sterilization, obviating the need for the lid 60.

At the instant of use, the lid 60 is peeled away, or, in the alternative arrangement, the sealed plastic bag is opened. The attached flexible tubing FT is extended beyond the bounds of the tray 48 to make connection with external processing items (see FIG. 10). The tubing FT carries appropriate couplers for this purpose. The tray 48 is moved along a vertical path for loading into the slot 27 and then a horizontal path for loading on the raised portion of the chassis panel 26, after which a simple motion of the door latching mechanism 30 aligns the entire fluid circuit 56 with the pumps, sensors, and clamps on the chassis panel 26. There is no area of blood or fluid contact that this outside the disposable circuit 56.

The source 46 supplying the cartridge 18 can comprise a company or business that manufactures the cartridge 18 or that otherwise distributes the cartridge 18 to the treatment location 12 on a sale, lease, or rental basis.

1. Fluid Circuit for Frequent Hemofiltration

Figure 11:
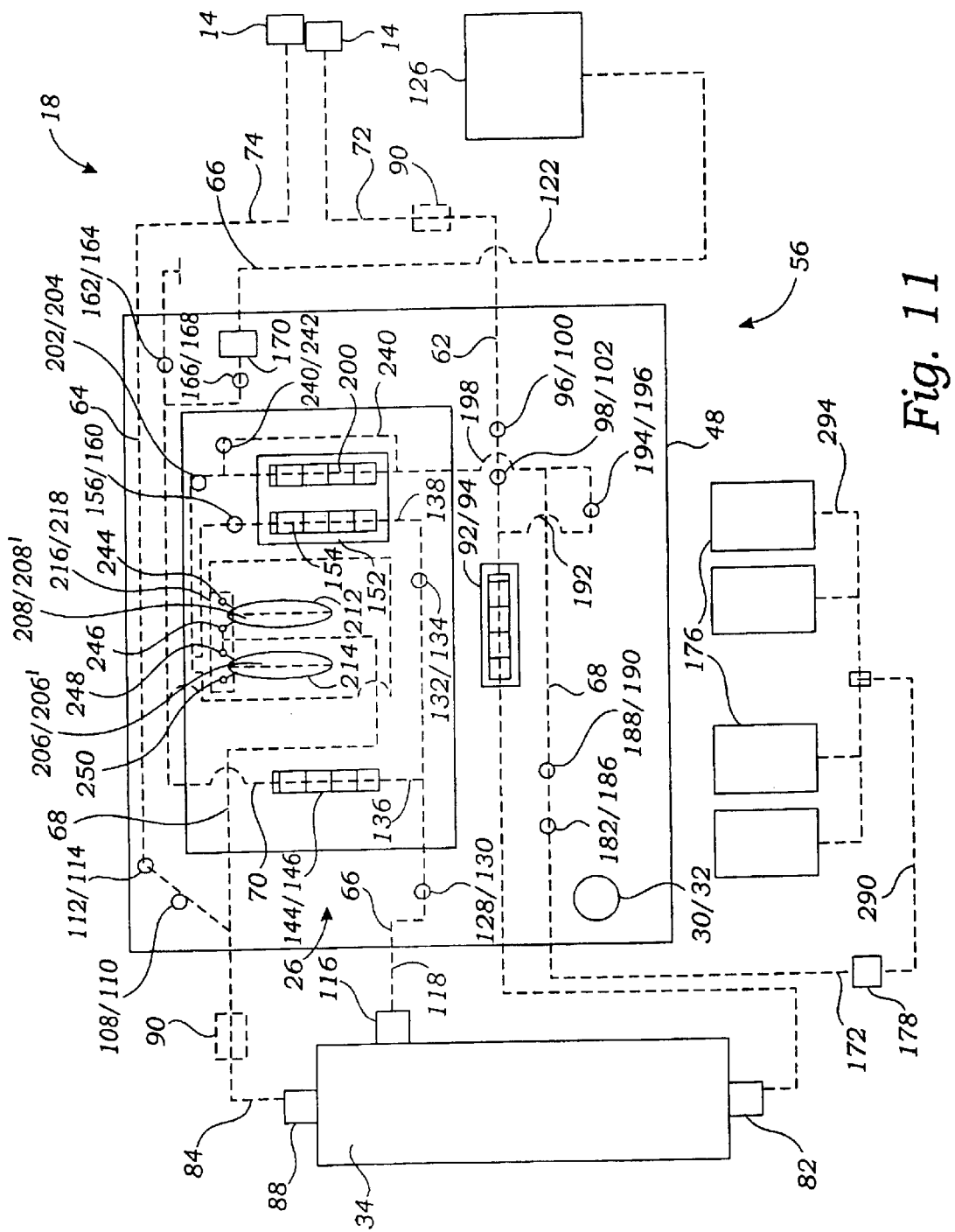
FIG. 11 is an embodiment of a fluid circuit that the cartridge shown in FIG. 10 can incorporate, being shown in association with the pumps, valves, and sensors of the hemofiltration machine shown in FIG. 2.

FIG. 11 shows a representative fluid circuit 56 that is well suited for carrying out frequent hemofiltration, and which can be incorporated into the cartridge 18 for interface with pumps, valves, and sensors arranged as a mirror image on the chassis panel 26.

The fluid circuit 56 couples the hemofilter 34 to several main fluid flow paths. The main fluid flow paths comprise an arterial blood supply path 62, a venous blood return path 64, a blood waste path 66, a replacement fluid path 68, and an ultrafiltration/fluid balancing path 70.

(i) Blood Supply and Return Paths

The arterial blood supply path 62 and venous blood return path 64 includes lengths of flexible tubing 72 and 74 that extend outside the tray 48 (see FIG. 10). As FIG. 10 shows, The paths 72 and 74 carry cannulas 76 at their distal ends (or connectors that enable connection to cannulas 76), to enable connection, respectively, to the person's arterial and venous access devices 14.

The arterial blood supply path 62 also includes a length of flexible tubing 78 (see FIG. 10) that extends outside the tray 48. The tubing 78 includes a distal connector 80 to couple to the blood inlet 82 of the hemofilter 34.

Likewise, the venous blood return path 64 includes a length of flexible tubing 84 that extends outside the tray 48. The tubing 84 includes a distal connector 86 to couple to the blood outlet 88 of the hemofilter 34.

Alternatively, the hemofilter 34 can be an integral part of the tray 48. In this arrangement, the arterial and venous blood paths 78 and 84 are supplied preconnected to the hemofilter 34.

The exterior tubing components of the arterial or venous blood paths can include injection sites 90. The sites can be used, e.g., to remove trapped air or to inject anticoagulant, medication, or buffers into the blood flows. The exterior tubing components of the arterial or venous blood paths can also include conventional pinch clamps, to facilitate patient connection and disconnection.

The remaining portions of arterial and venous blood paths 62 and 64 are contained in the circuit 56 held within the tray 48. The blood pump 92 of the machine 16 engages a pump header region 94 in the arterial blood supply path 62 within the tray 48 upstream of the hemofilter 34, to convey blood into and through the hemofilter 34. An arterial blood clamp 96 and a patient connection-disconnection (air bubble detector) sensor 98 on the machine 16 engage a clamp region 100 and a sensor region 102 in the arterial blood supply path 62 within the tray 48 upstream of the blood pump 92. Alternatively, an air bubble sensor (not shown) can be located downstream of the blood pump 92 and upstream of the hemofilter 34.

The placement of the air sensor 98 upstream of the hemofilter 34 allows air bubbles to be detected prior to entering the hemofilter 34. In the hemofilter 34, air bubbles break up into tiny micro-bubbles, which are not as easily detected. Placement of the air sensor 98 upstream of the hemofilter 34 also serves the additional purpose of detecting air when the blood pump 92 is operated in reverse, to rinse back blood to the patient, as will be described later.

An air detector 108 on the machine 16 engages a sensing region 110 in the venous blood return path 64 within the tray 48 downstream of the hemofilter 34. A venous clamp 112 on the machine 16 engages a clamp region 114 in the venous blood return path 64 within the tray 48 downstream of the air detector 108.

(ii) Blood Waste Path

The membrane (not shown) located in the hemofilter 34 separates waste including liquid and uremic toxins from the blood. A waste outlet 116 conveys waste from the hemofilter 34.

The blood waste path 66 includes a length of flexible tubing 118 (see FIG. 10) that extends beyond the tray 48. The tubing 118 carries a distal connector 120 to couple to the waste outlet 116 of the hemofilter 34. Alternatively, when the hemofilter 34 is integrated in the tray 48, the waste path 66 can be supplied preconnected to the hemofilter 34.

The waste path 66 also includes a length of flexible tubing 122 that extends beyond the tray 48. The tubing 122 carries a connector 124 to couple to a waste bag 126 or an external drain. Alternatively, the waste bag 126 can be preconnected to the tubing 122.

The remainder of the waste path 66 is contained within the circuit 56 inside the tray 48. A blood leak detector 128 on the machine 16 engages a sensor region 130 in the waste path 66 downstream of the hemofilter 34. A waste pressure sensor 132 on the machine 16 engages another sensor region 134 in the waste path 66 downstream of the blood leak detector 128.

Within the tray 48, the waste path 66 branches into an ultrafiltration path 136 and a balancing path 138. The ultrafiltration branch path 136 bypasses in-line containers 212 and 214 of the circuit 56. The ultrafiltration pump 144 on the machine 16 engages a pump header region 146 in the ultrafiltration branch path 136 within the tray 48. The waste balancing branch path 138 communicates with the in-line containers 212 and 214. The waste and replacement fluid pump 152 on the machine 16 engages a pump header region 154 in the waste balancing branch path 138 within the tray 48 upstream of the in-line containers 212 and 214. A pressure sensor 156 on the machine 16 engages a sensor region 160 in the waste balancing branch path 138 within the tray 48 between the waste and replacement fluid pump 152 and the in-line containers 212 and 214. The pressure sensor 156 senses the fluid pressure required to convey replacement fluid into the venous return line. This resistance to the flow of replacement fluid is the venous blood pressure. The pressure sensor 156 in the waste fluid path 138 thereby serves to sense the venous blood pressure.

A flush clamp 162 engages a clamp region 164 in the waste path 66 within the tray 48 downstream of the in-line containers 212 and 214. A waste clamp 166 engages a clamp region 168 in the waste path 66 downstream of the flush clamp 162. The circuit 56 in the tray 48 also can include an air break 170, which communicates with the waste path 66 downstream of the waste clamp 166. The air break 170 prevents back flow of contaminants into the circuit 56 from the waste bag 126 or drain.

(iii) Replacement Fluid Path

The replacement fluid path 68 includes a length of flexible tubing 172 that extends outside the tray 48. The tubing 172 includes a distal connector 174 or connectors that enable connection to multiple containers of replacement fluid 176. As will be described later, the tubing 172 can also include an in-line 0.2 m sterilizing filter 178 to avoid contamination of the circuit 56.

The containers 176 together typically hold from 8 to 20 combined liters of replacement fluid, depending upon the fluid removal objectives of the particular frequent hemofiltration procedure. The replacement fluid is also used to prime the fluid circuit 56 at the outset of a treatment session and to rinse back blood to the patient at the end of a treatment session.

The remainder of the replacement fluid path 68 is contained in the circuit 56 within the tray 48. Sensing region 186 in the replacement fluid path 68 inside the tray 48 engages a replacement fluid flow rate detector 182 on the machine 16. A clamping region 190 in the replacement fluid path 68 inside the tray 48 engages a replacement fluid clamp 188 on the machine 16.

Within the tray 48, the replacement fluid path 68 includes a priming or bolus branch path 192 that communicates with the arterial blood supply path 62. A clamping region 196 in the priming branch path 192 engages a priming clamp 194 on the machine 16.

Within the tray 48, the replacement fluid path 68 also includes a balancing branch path 198 that communicates with the venous blood return path 64, via the in-line containers 212 and 214. A pump header region 200 in the balancing replacement branch path 198 engages the waste and fluid replacement pump 152 on the machine 16 upstream of the in-line containers 212 and 214.

In the illustrated embodiment, the waste and fluid replacement pump 152 comprises a dual header pump, simultaneously engaging the two pump header regions 154 and 200 on the waste path 66 and the replacement fluid path 68. A sensor region 204 in the balancing replacement branch path 198 engages a pressure sensor 202 on the machine 16 between the waste and replacement fluid pump 152 and the in-line containers 212 and 214. The pressure sensor 202 senses the pressure required to convey waste fluid into the waste return line. This resistance to the flow of waste fluid is the waste line pressure. The pressure sensor 202 in the replacement fluid path 198 thereby serves to sense the waste line pressure. Similarly, as already described, the pressure sensor 156 in the waste fluid path 138 serves to sense the venous blood pressure.

(iv) Ultrafiltration/Fluid Balancing Path

The ultrafiltration waste branch path 136 within the tray 48, which bypasses the in-line containers 212 and 214 of the circuit 56, accommodates transfer of a prescribed volume of waste to the waste bag 126, without an offsetting volume of replacement fluid. The circuit 56 thereby is capable of performing an ultrafiltration function.

The balancing waste branch path 138 and the balancing replacement branch path 198 pass through the in-line containers 212 and 214 in the circuit 56 contained within the tray 48. The in-line containers 212 and 214 transfer a volume of replacement fluid to the venous blood return path 64 in proportion to the volume of waste fluid removed, except for the volume making up the ultrafiltration volume loss. The circuit 56 is thereby capable of performing a fluid balancing function in addition to the ultrafiltration function.

Figure 12A:
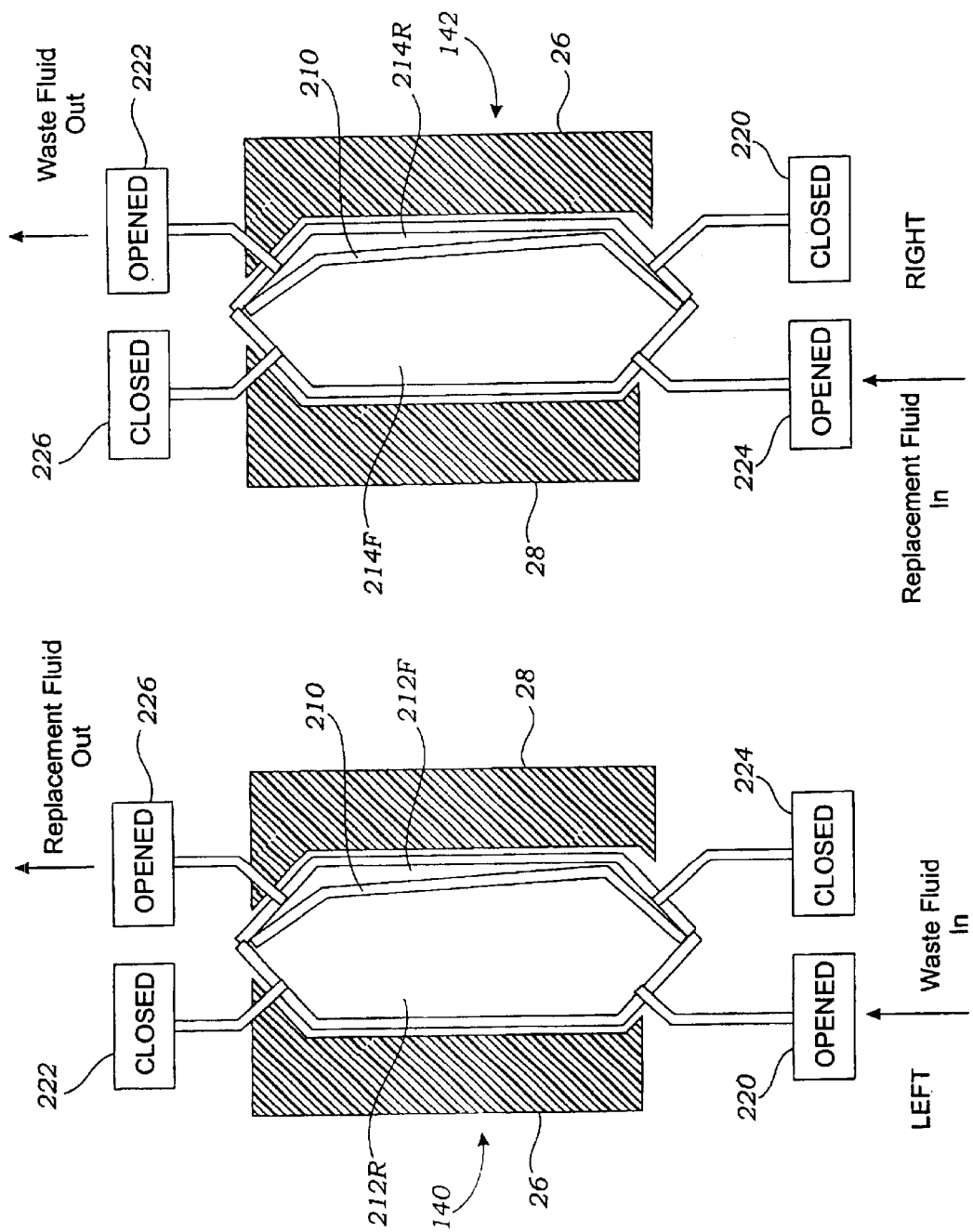
FIGS. 12A and 12B are largely schematic side section views of one embodiment of fluid balancing compartments that can form a part of the circuit shown in FIG. 11, showing their function of volumetrically balancing replacement fluid with waste fluid.
Figure 12B:
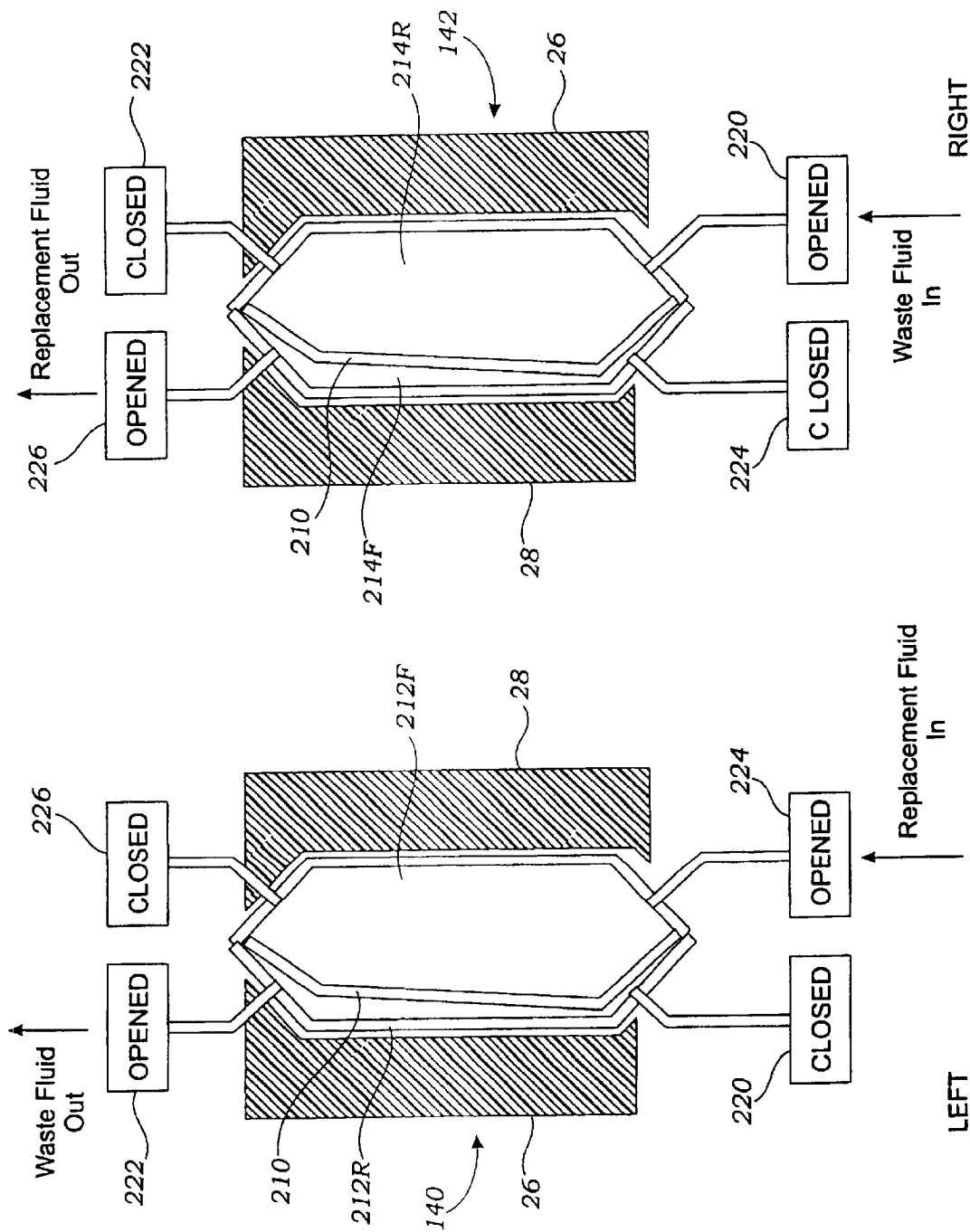

In the illustrated embodiment, the machine 16 and circuit 56 carry out the fluid balancing function volumetrically, without weight sensing. More particularly, the registered chambers 206/206' and 208/208' on the chassis panel 26 and door 28 of the machine 16 receive the in-line containers 212 and 214 when the tray 48 is mounted on the chassis panel 26. The registered chambers 206/206' and 208/208' mutually impose volumetric constraints on the in-line containers 212 and 214, to define a maximum interior volume for each of the on-line containers 212 and 214. In the illustrated embodiment, when facing the chassis panel 26, the container 212 is situated on the left side (in registered chambers 206/206') and the container 214 is situated on the right side (in registered chambers 208/208'). FIGS. 12A and 12B show one embodiment of the right and left orientation of the containers 212 and 214, with the containers 212 and 214 also shown in side section.

In the embodiment shown in FIGS. 12A and 12B, each in-line container 212 and 214 is itself divided along their midline from front to back by an interior flexible wall 210, to form four compartments. As FIG. 12A and 12B show, two of the compartments face the door 28, and are thus designated as front compartments 212F and 214F. The other two compartments face the chassis panel 26, and will thus be designed as rear compartments 212R and 214R.

Each in-line container 212 and 214 has a waste side compartment communicating with waste path 66 and a replacement side compartment communicating with the replacement fluid path 68. In the illustrated embodiment, the circuit 56 establishes communication between the balancing waste branch path 138 and the rear compartments 212R and 214R (which will also be called the waste side compartments). The circuit 56 also establishes communication between the balancing replacement branch path 198 and the front compartments 212R and 214R (which will also be called the replacement side compartments). In the embodiment illustrated in FIGS. 12A and 12B, fluid enters the compartments from the bottom and exits the compartments from the top. Other flow paths into and from the compartments can be established, as will be described later.

The machine 16 includes an inlet valve assembly 216 and an outlet valve assembly 218 on the chassis panel 26, located in association with the chambers 206 and 208. The circuit 56 in the tray 48 likewise includes, for each in-line container 212 and 214, an inlet clamp region 220 and an outlet clamp region 222, which govern flow into and out of the waste side compartments 212R and 214R. The circuit 56 in the tray 48 also includes, for each in-line container 212 and 214, an inlet clamp region 224 and an outlet clamp region 226, which govern flow into and out of the replacement side compartments 212F and 214F.

When the tray 48 is mounted on the chassis panel 26, the inlet and outlet valve assemblies 216 and 218 on the machine 16 engage the corresponding waste and replacement fluid inlet and outlet clamp regions 220, 222, 224, 226 in the circuit 56. The machine 16 toggles the operation of inlet and outlet valve assemblies 216 and 218 to synchronize the flow of fluids into and out of the waste side and replacement side compartments of each in-line container 212 and 214.

More particularly, for a given in-line container 212 and 214, in a first valve cycle (see FIG. 12A), the waste side inlet valve 220 is opened while the waste side outlet valve 222 is closed. Waste fluid is conveyed by operation of the waste and replacement pump 152 from the waste path 66 into the waste side compartment of the given in-line container 212 and 214. Simultaneously, for the same in-line compartment 212 and 214, the replacement side inlet valve 224 is closed and the replacement side outlet valve 226 is opened, so that the incoming flow of waste in the waste side compartment displaces the interior wall 210 to express a like volume of replacement fluid from the replacement side compartment into the venous blood return path 64.

In a subsequent cycle for the same in-line container 212 and 214, an opposite valve action occurs (see FIG. 12B). The replacement side inlet valve 224 is opened and the replacement side outlet valve 226 is closed, and replacement fluid is conveyed into the replacement side compartment from the replacement fluid path 68. The incoming replacement fluid displaces the interior wall 210 to express a like volume of waste fluid from the waste side compartment to the waste bag 126 (the waste side inlet valve 220 now being closed and the waste side outlet valve 222 now being opened).

As FIGS. 12A and 12B show, the valve assemblies work in tandem upon the two in-line containers 212 and 214, with one container 140 receiving waste and dispensing replacement fluid, while the other container 142 receives replacement fluid and dispenses waste, and vice versa. In this way, the circuit 56 provides a continuous, volumetrically balanced flow of waste fluid to the waste bag 126 and replacement fluid to the venous blood return path 64.

2. A Circuit Contained in a Double Panel Bag

Figure 13A:
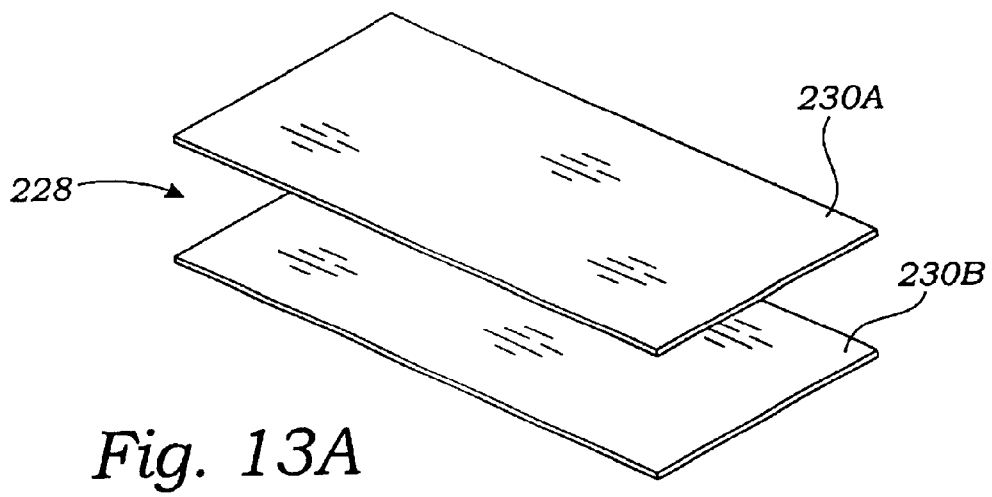
FIGS. 13A, 13B, and 13C are perspective views of a bag configured with a pattern of seals and folded over to define a overlaying flexible fluid circuit that can be placed in a fluid processing cartridge of a type shown in FIG. 11.
Figure 13B:
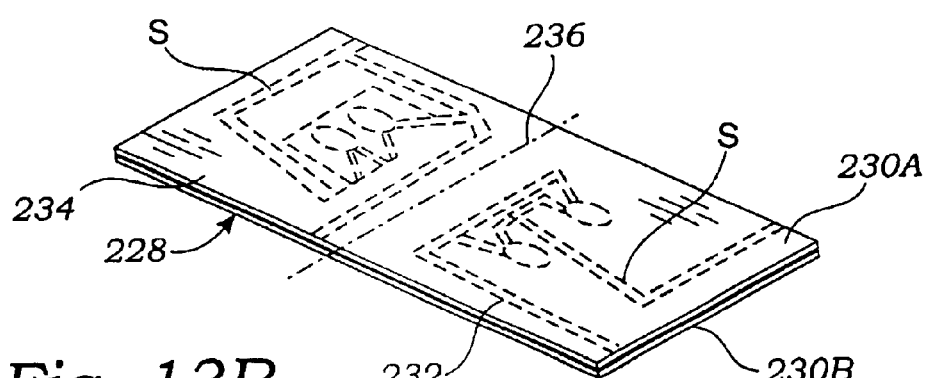
Figure 13C:
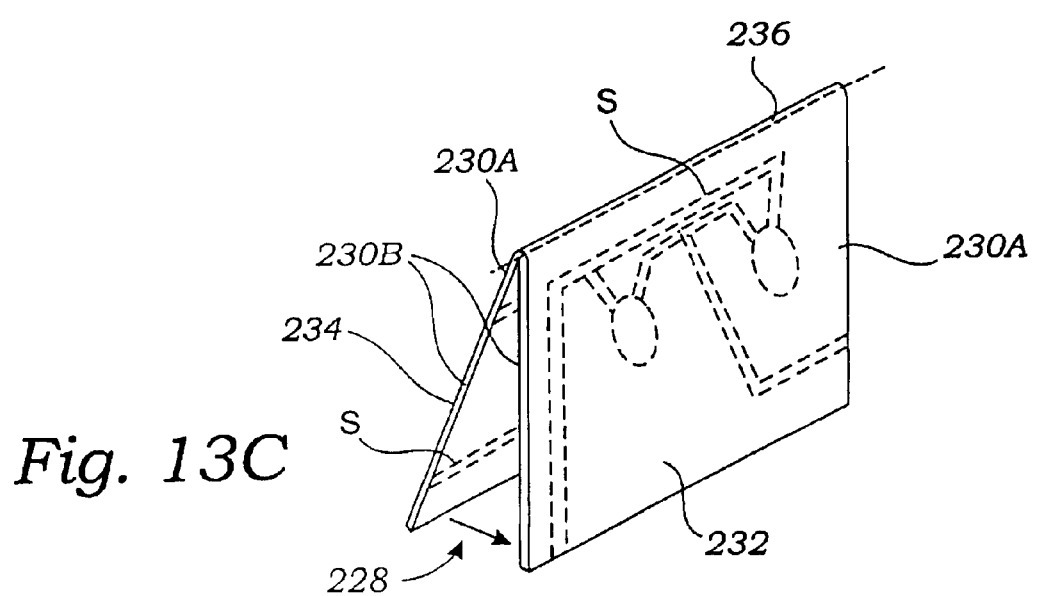

The function of the fluid circuit 56 shown in FIGS. 11, 12A, and 12B can be realized in various ways. FIGS. 13A to 13C show a fluid circuit bag 228 made from two overlaying sheets 230A and 230B of flexible medical grade plastic, e.g., poly vinyl chloride (see FIG. 13A). When laid flat (see FIG. 13B), the bag 228 defines first and second panels 232 and 234 divided along a midline 236. By folding the bag 228 about its midline 236 (see FIG. 13C), the first and second panels 232 and 234 are brought into registration in a reverse facing relationship, with one panel 232 comprising the front of the bag 228 and the other panel 234 comprising the back of the bag 228.

The first and second panel 232 and 234 each includes an individual pattern of seals S formed, e.g., by radio frequency welding. The seals S form fluid flow paths, including the in-line containers 212 and 214, peristaltic pump header regions, the sensor regions, and clamp regions previously described. The flow paths formed by the pattern of seals S can comprise all or part of the circuit 56. Pump header tubing lengths 155, 145, and 201 are sealed in placed within the seal pattern S to form the pump regions 154, 146, and 201, respectively.

Figure 14:
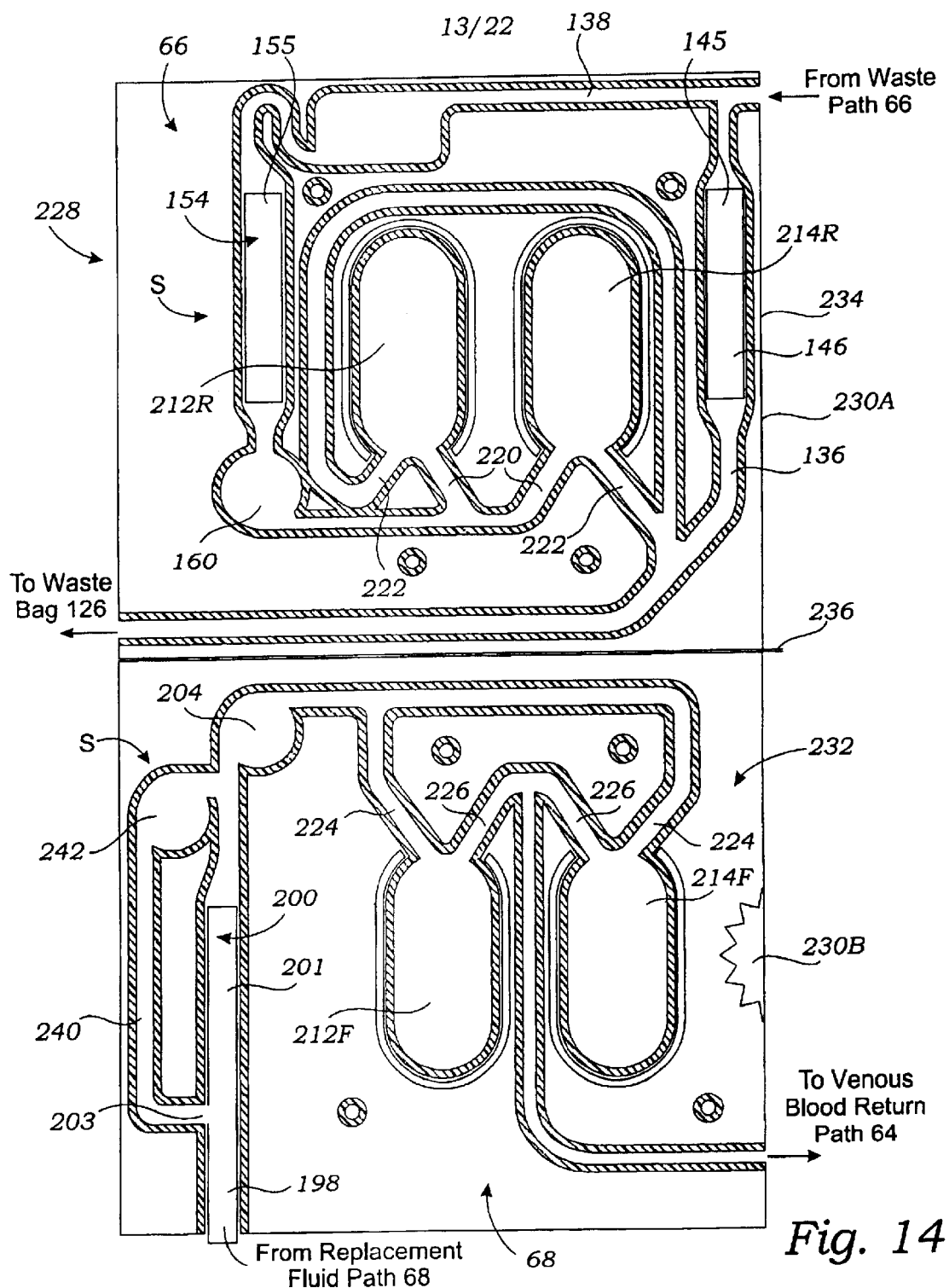
FIG. 14 is a plane view of the pattern of seals that the bag shown in FIGS. 13A, 13B, and 13C carries, before the bag is folded over on itself.

In the illustrated embodiment, as FIG. 14 shows, the seals S on the first panel 232 are configured to form the flow paths of the circuit 56 through which replacement fluid is conveyed from the replacement fluid path 68 to the venous blood return path 64, including the left and right front-facing replacement fluid compartments 212F and 214F. The seals S on the second panel 234 are configured to form the flow paths of the circuit 56 through which waste fluid is conveyed from the waste path 66 to the waste bag 126 or drain, including the left and right rear-facing waste fluid compartments 212R and 214R. Seals S form four individual containers, two containers 212F and 214F on the panel 232, and two containers 212R and 214R on the panel 234.

Figure 15:
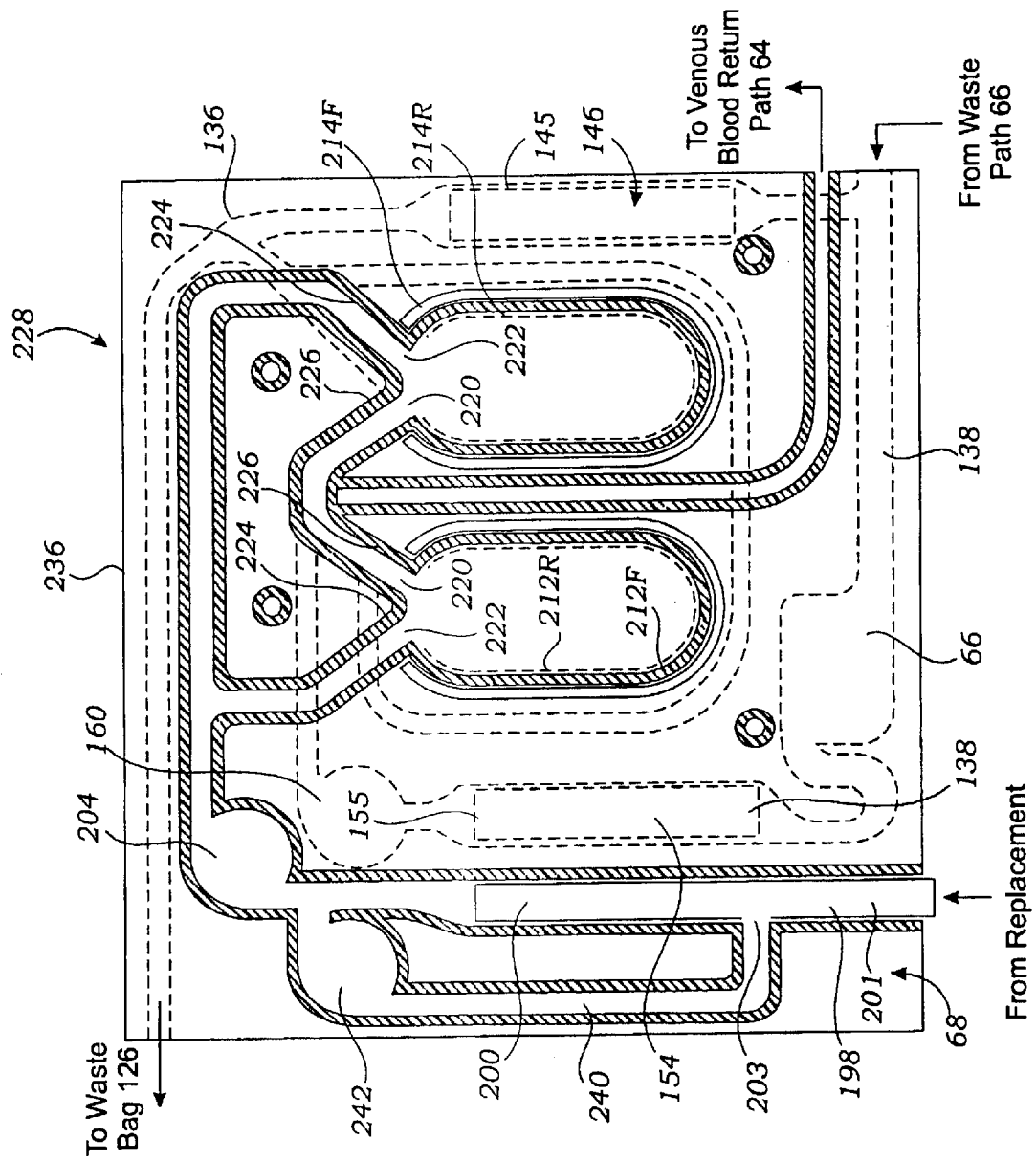
FIG. 15 is a plane view of the overlaying fluid circuit that the bag shown in FIG. 14 forms after having been folded over on itself.

Once the seal patterns S are formed, the bag 228 is folded over about its midline 236 (see FIG. 15). The bag 228 places in close association or registry the waste and replacement fluid paths 66 and 68 of the circuit 56. The replacement fluid paths 68 of the circuit 56 occupy the front panel 232 of the bag 228, and the waste paths 66 of the circuit 56 occupy the back panel 234 of the bag 228 (or vice versa, depending upon the desired orientation of the bag 228).

In use, the folded over bag 228 is contained in the base 50 of the tray 48, with portions exposed through cutouts 58 in the insert 51 for engagement with the machine peristaltic pumps, sensing elements, and clamping elements, in the manner shown in FIG. 10. The remaining portions of the circuit 56 not contained within the bag 228 are formed of tubing and fit into preformed areas in the base 50 of the tray 48 (or formed within another bag) and coupled in fluid communication with the flow paths of the bag 228, to complete the circuit 56 shown in FIG. 10.

The flow paths formed on the first panel 232 include the balance replacement fluid paths 198, which lead to and from the replacement side compartments 212F and 214F. In the tray 48, the replacement side compartments 212F and 214F rest in recesses in the tray base 50. Cutouts 58 in the insert 51 expose the pump header regions 200 and 154, to engage the peristaltic waste and replacement pump 152 on the machine 16; the inlet clamp regions 224, to engage the inlet valve assembly 216 on the machine 16 to control inflow of replacement fluid into the replacement side compartments 212F and 214F; and the outlet clamp regions 226, to engage the outlet valve assembly 218 on the machine 16 to control outflow of replacement fluid from the replacement side compartments 212F and 214F. The cutouts 58 also expose the sensor region 204, to engage the pressure sensor 202 downstream of the waste and replacement pump 152, and a pressure relief path 240 with exposed pressure relief bypass valve 242, the purpose of which will be described later. A small opening 203 formed in the pump header tubing 201 opens communication with the relief path 240.

The flow paths formed on the second panel 234 (shown in phantom lines in FIG. 15) include the waste path 138 that lead to and from the waste side compartments 212R and 214R (for fluid balancing) and the waste path 136 that bypasses the waste side compartments 212R and 214R (for ultrafiltration). As FIG. 15 shows, when the bag 228 is folded over in the tray 48, the waste compartments 212R and 214R on the waste panel 234 and the replacement compartments 212F and 214F on the replacement panel 232 overlay, so both are exposed through the cutout 58 in the insert for registry as a unit with the chambers 206 and 208 on the chassis panel 26.

The flow paths on the waste panel 234 also include the exposed waste inlet clamp regions 220, to engage the valve assembly 218 to control inflow of waste fluid into the waste compartments 212R and 214R, and the exposed waste outlet clamp regions 222, to engage the valve assembly 216 to control outflow of waste fluid from the waste compartments 212R and 214R. When the bag 228 is folded over in the tray 48, the inlet clamp regions of the waste compartments 212R and 214R formed on the waste panel 234 overlay the outlet clamp regions of the replacement compartments 212F and 214F formed on the replacement panel 232, and vice versa.

The flow paths also includes an exposed pump header region 154, to engage the peristaltic waste and replacement pump 152. When the bag 228 is folded over in the tray 48, the exposed pump header regions 200 and 154 on the replacement and waste panels 232 and 234 lay side-by-side, to accommodate common engagement with the dual header waste and replacement pump 152. The flow paths also include the sensor region 160, to engage the pressure sensor 156 downstream of the waste and replacement fluid pump 152.

The flow paths also include the pump header region 146, to engage the peristaltic ultrafiltration pump 144. When the bag 228 is folded over in the tray 48, the exposed pump header region 146 for the ultrafiltration pump 144 is spaced away from the other pump header regions of the circuit 56.

In FIGS. 12A and 12B, the entry paths serving the waste and replacement compartments are located at the bottom, while the exit paths serving the waste and replacement compartments are located at the top. This configuration facilitates priming of the compartments. Still, the spaced apart configuration requires eight valve assemblies.

Figure 16:
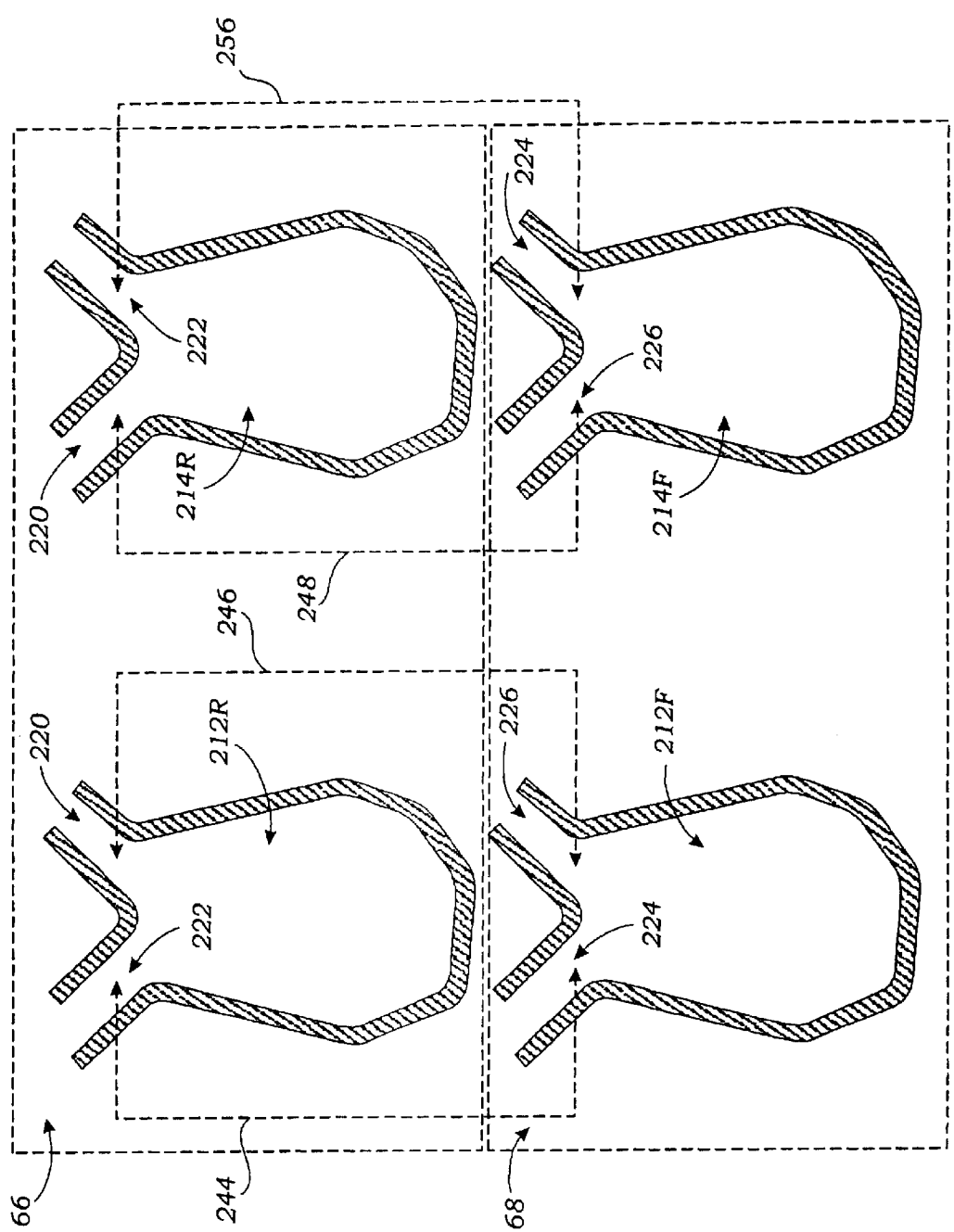
FIG. 16 is a largely schematic side section view of the overlaying fluid balancing compartments that are part of the circuit shown in FIG. 15, showing their function of volumetrically balancing replacement fluid with waste fluid.

In FIG. 16, the entry and exit paths serving the waste and replacement compartments are all located at the top. Priming is still achieved, as the paths are top-oriented. Furthermore, due to the folded-over configuration of the bag itself, the clamping regions 220, 222, 226 can be arranged overlay one another. The overlaying arrangement of the clamping regions 220, 222, 224, and 226 serving the waste and replacement compartments simplifies the number and operation of the inlet and outlet valve assemblies 216 and 218 on the machine 16. Since the inlet clamp regions 224 for the replacement compartments 212F and 214F overlay the outlet clamp regions 222 for the waste compartments 212R and 214R, and vice versa, only four clamping elements 244, 246, 248, 250 need be employed to simultaneously open and close the overlaying eight clamp regions (see FIG. 16). By further stacking (not shown) of the compartments, the clamping elements could be reduced to two.

As FIG. 16 shows, the first clamping element 244 is movable into simultaneous clamping engagement with the inlet clamp region 224 of the left replacement compartment 212F (on the replacement panel 232) and the outlet clamp region 222 of the left waste compartment 212R (on the waste panel 234), closing both. Likewise, the fourth clamping element 250 is movable into simultaneous clamping engagement with the inlet clamp region 224 of the right replacement compartment 214F (on the replacement panel 232) and the outlet clamp region 222 of the right waste compartment 214R (on the waste panel 234), closing both.

The second clamping element 246 is movable into simultaneous clamping engagement with the outlet clamp region 226 of the left replacement compartment 212F (on the replacement panel 232) and the inlet clamp region 220 of the left waste compartment 212R (on the waste panel 232), closing both. Likewise, the third clamping element 248 is movable into simultaneous clamping engagement with the outlet clamp region 226 of the right replacement compartment 214F(on the replacement panel 232) and the inlet clamp region 220 of the right waste compartment 214R (on the waste panel 234), closing both.

The machine 16 toggles operation of the first and third clamping elements 244, 248 in tandem, while toggling operation the second and fourth clamping elements 246, 250 in tandem. When the first and third clamping elements 244, 248 are operated to close their respective clamp regions, replacement fluid enters the right replacement compartment 214F to displace waste fluid from the underlying right waste compartment 214R, while waste fluid enters the left waste compartment 212R to displace replacement fluid from the overlaying left replacement compartment 212F. When the second and fourth clamping elements 246, 250 are operated to close their respective clamp regions, replacement fluid enters the left replacement compartment 212F to displace waste fluid from the underlying left waste compartment 212R, while waste fluid enters the right waste compartment 214R to displace replacement fluid from the overlaying right replacement compartment 214F.

Figure 17:
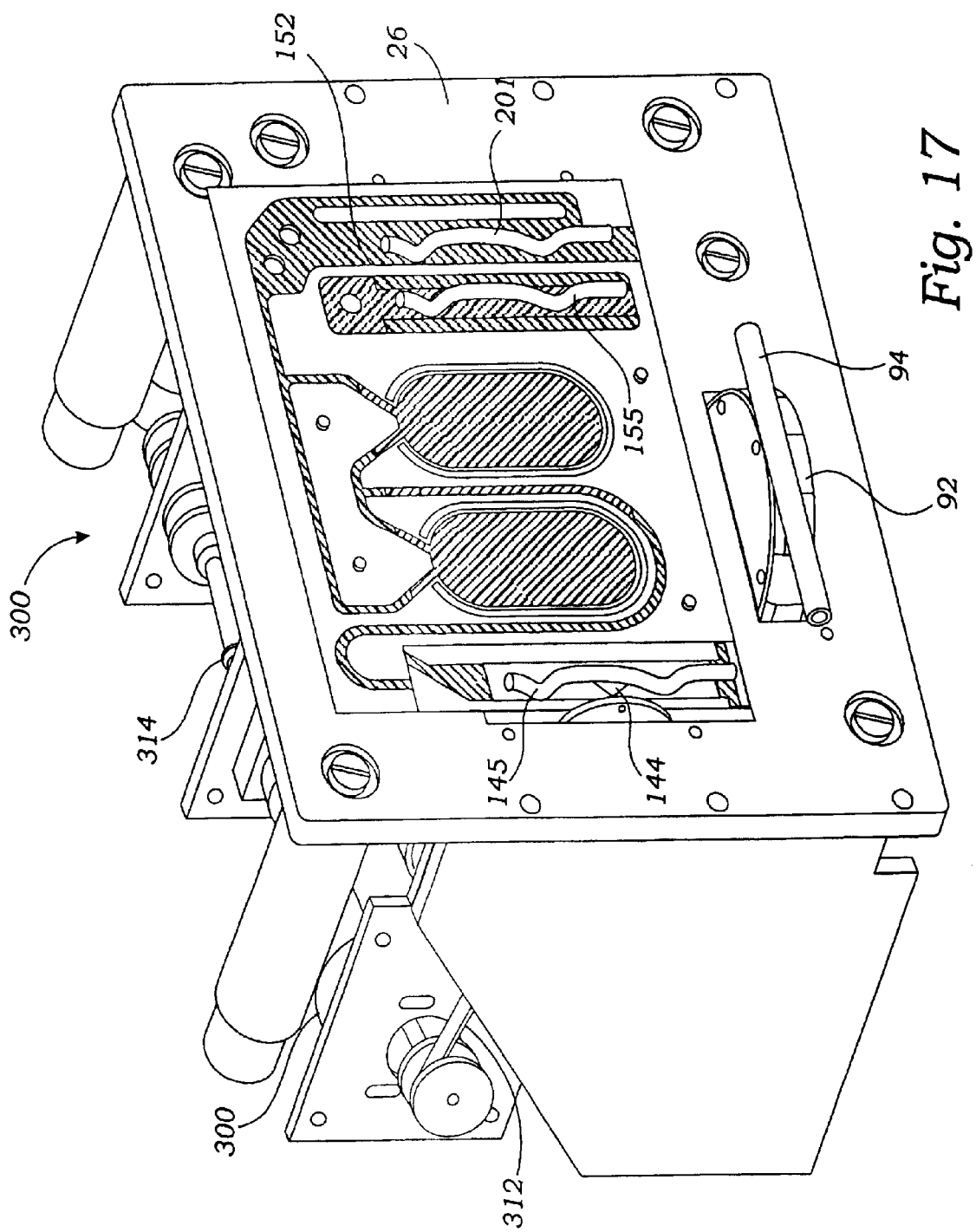
FIG. 17 is a front perspective view of an embodiment of a chassis panel that the hemofiltration machine shown in FIG. 2 can incorporate.
Figure 18:
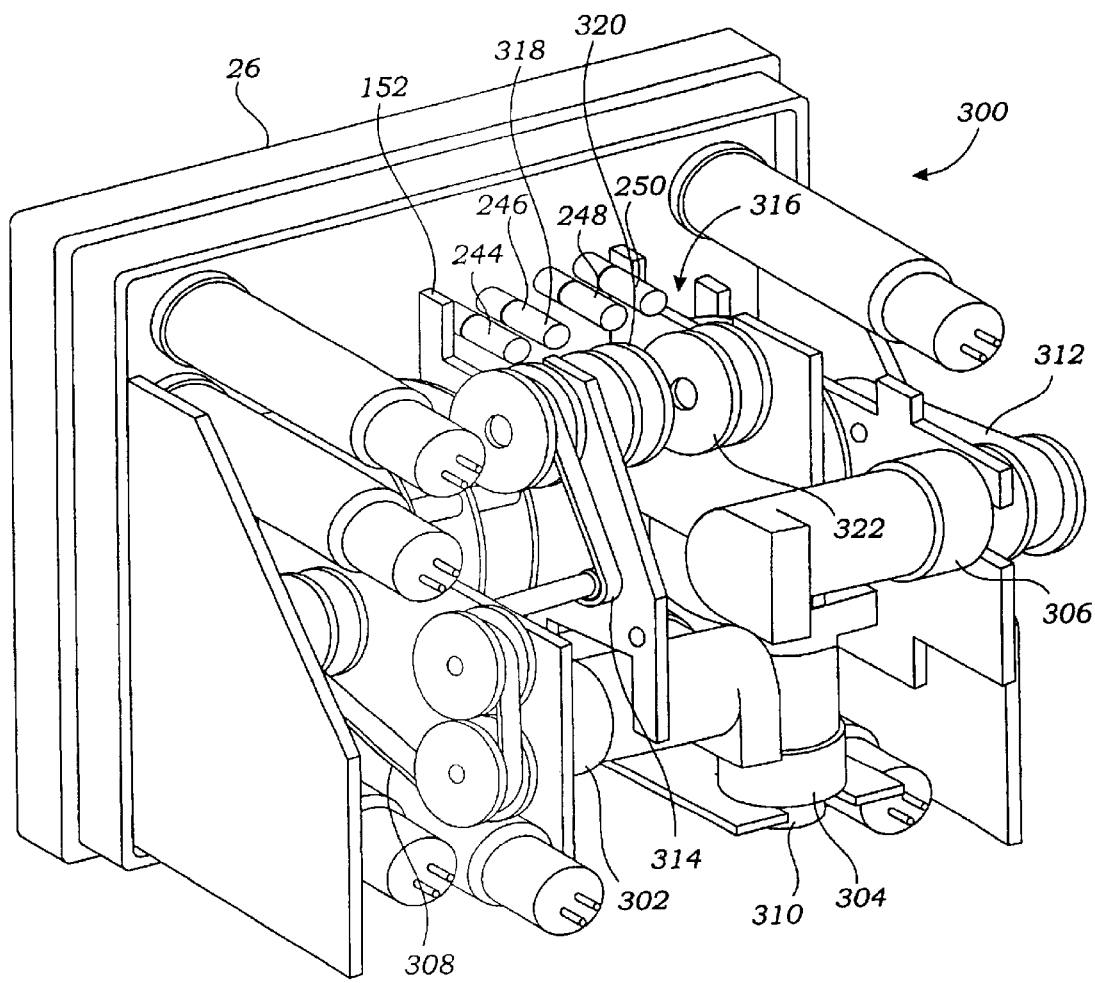
FIG. 18 is a back perspective view of the chassis panel shown in FIG. 17, showing the mechanical linkage of motors, pumps, and valve elements carried by the chassis panel.

FIGS. 17 and 18 show a mechanically linked pump and valve system 300 that can be arranged on the chassis panel 26 and used in association with the layered fluid circuit bag 228 shown in FIG. 15.

The system 300 includes three electric motors 302, 304, and 306. The first motor 302 is mechanically linked by a drive belt 308 to the dual header waste and replacement pump 152, previously described. The second motor 304 is mechanically linked by a drive belt 310 to the blood pump 92, also previously described. The third motor 306 is mechanically linked by a drive belt 312 to the ultrafiltration pump 144, also as previously described.

A drive belt 314 also mechanically links the first motor to the first, second, third, and fourth clamping elements 244, 246, 248, and 250, via a cam actuator mechanism 316. The cam actuator mechanism 316 includes, for each clamping element 244, 246, 248, and 250 a pinch valve 318 mechanically coupled to a cam 320. The cams 320 rotate about a drive shaft 322, which is coupled to the drive belt 314.

Rotation of the cams 320 advances or withdraws the pinch valves 318, according to the surface contour machined on the periphery of the cam 320. When advanced, the pinch valve 318 closes the overlying clamp regions of the fluid circuit bag 228 that lay in its path. When withdrawn, the pinch valve 318 opens the overlying clamp regions.

The cams 320 are arranged along the drive shaft 322 to achieve a predetermined sequence of pinch valve operation. During the sequence, the rotating cams 320 first simultaneously close all the clamping elements 244, 246, 248, and 250 for a predetermined short time period, and then open clamping elements 244 and 248, while closing clamping elements 246 and 250 for a predetermined time period. The rotating cams 320 then return all the clamping elements 244, 246, 248, and 250 to a simultaneously closed condition for a short predetermined time period, and then open clamping elements 246 and 250, while closing clamping elements 244 and 248 for a predetermined time period.

The sequence is repeated and achieves the balanced cycling of replacement fluid and waste fluid through the containers 212 and 214, as previously described. A chamber cycle occurs in the time interval that the valve elements 244, 246, 248, and 250 change from a simultaneously closed condition and return to the simultaneously closed condition.

The cam actuator mechanism 316 mechanically links the clamping elements 244, 246, 248, and 250 ratiometrically with the first motor 302. As the motor 302 increases or decreases the speed of the dual header waste and replacement pump 152, the operation of the clamping elements 244, 246, 248 and 250 increases or decreases a proportional amount.

In a preferred embodiment, the ratio is set so that the flow rate per unit time through the waste pump header region 154 (i.e., through waste path 66) approximately equals three-fourths of the volume of the waste compartment 212R/214R, while maintaining the cycle rate at less than 10 cycles per minute. For example, if the chamber volume is 20 cc, the cycle occurs after 15 to 17 cc of waste fluid enters the compartment.

In the illustrated embodiment, the waste pump header region 154 is made smaller in diameter than the replacement fluid header region 200. Thus, during operation of the dual header pump 152, the flow rate through the replacement fluid header region 200 (through replacement fluid path 68) will always be larger than the flow rate through the waste pump header region 154 (through waste path 68). Due to the high flow rate through the replacement fluid path 68, a pressure relief path 240 with pressure relief bypass valve 242 is provided, to prevent overfilling. In the illustrated embodiment, the valve 242 is a mechanically spring biased pressure regulator, and serves the pressure regulation and bypass function of the machine 16.

In this arrangement, the in-line compartment that receives waste fluid will fill to approximately three-fourths of its volume during each cycle, displacing an equal amount of replacement fluid from its companion compartment. At the same time, the other in-line compartment that receives replacement fluid will fill completely. If the compartment completely fills with replacement fluid before the end of the cycle, the pressure relief bypass valve 242 will open to circulate replacement fluid through the relief path 240 to prevent overfilling. During the next cycle, waste fluid in the compartment will be completely displaced by the complete fill of replacement fluid in its companion compartment.

The provision of a higher flow rate in the replacement fluid path also facilitates initial priming (as will be described later). Only several chamber cycles are required to completely prime the in-line containers 212 and 214 with replacement fluid before fluid balancing operations begin.

The pump and valve system 300 used in association with the layered fluid circuit bag 228 achieves accurate fluid balancing during frequent hemofiltration. Due to the smaller volumes of replacement fluid required during each frequent hemofiltration session, slight variations that may occur (e.g., plus or minus 5%) between fluid volume removed and fluid volume replaced do not lead to large volume shifts. As a result of accurate balancing of small fluid volumes, a person undergoing frequent hemofiltration does not experience significant day-to-day swings in body fluid volume, and more precise control of the person's body fluid and weight can be achieved.

C. Supplying Ancillary Materials

The system 10 further includes a source 252 or sources that supply ancillary materials 20 to the treatment location 12 for use in association with the cartridge 18 and machine 16. The ancillary materials 20 include the replacement fluid containers 176, as prescribed by the person's physician.

The ancillary materials 20 may also include an anticoagulant prescribed by a physician. However, anticoagulant may not be required for every person undergoing frequent hemofiltration, depending upon treatment time, treatment frequency, blood hematocrit, and other physiologic conditions of the person.

The ancillary materials 20 can also include the hemofilter 34, although, alternatively, the tray 48 can carry the hemofilter 34, or the hemofilter 34 can comprise an integrated component of the cartridge 18.

Through operation of the machine 16, cartridge 18, and ancillary materials 20 supplied by the system 10, the person's blood is conveyed through the hemofilter 34 for removal of waste fluid containing urea and other toxins. Replacement fluid is exchanged for the removed waste fluid, to maintain the person's electrolyte balance and acid/base balance. The replacement fluid is also balanced against an additional waste fluid removal, to yield a net ultrafiltration loss, as prescribed by the person's physician.

The composition of an optimal replacement fluid solution usable during frequent hemofiltration consist of a balanced salt solution containing the major cationic and anionic plasma constituents, including bicarbonate or another anion from which net bicarbonate can be generated by metabolism. Specific cationic substances removed by frequent hemofiltration that require replacement typically include sodium, potassium and calcium. Specific anionic substances removed by frequent hemofiltration that require replacement include chloride and either bicarbonate or another anion that can be metabolized into bicarbonate, such as acetate, citrate, or, typically, lactate.

The replacement fluid for frequent hemofiltration should exclude phosphorus and other anionic substances. These materials typically accumulate in undesirable amounts in persons experiencing renal failure and are either difficult to remove in large amounts during hemofiltration or are safely removed without need for specific replacement.

The concentration of sodium in a replacement fluid for frequent hemofiltration should fall slightly below that of the typical blood filtrate concentration of 135 to 152 meq/liter. The optimal range for sodium in the replacement fluid for frequent hemofiltration is 128–132 meq/liter, and typically 130 meq/liter. This concentration allows for a net sodium removal during frequent hemofiltration sessions, which is easily tolerated due to the smaller replacement fluid volumes necessary for frequent hemofiltration. This concentration also results in a minimal net drop in serum osmolality, so as to decrease extracellular volume to a extent sufficient to maintain euvolemia while ameliorating thirst in the person undergoing frequent hemofiltration.

The metabolism of calcium is quite complicated and much less straightforward than sodium. Thus, the optimal concentration in a replacement fluid for frequent hemofiltration should be much closer to the normal physiologic range of calcium in plasma, i.e., in a range of 2.5 to 3.5 meq/liter, and typically 2.7 meq/liter. This calcium concentration range is required to prevent tetany, which can result from excessive removal of ionized calcium, while removing excessive serum calcium that may result from the oral calcium supplements and phosphorus binders frequently used by persons requiring hemofiltration.

Selecting an optimal concentration of potassium in a replacement fluid for frequent hemofiltration is important. Typically, the potassium concentrations selected for replacement fluids used during infrequent hemofiltration (3 times a week or less) or during hemodialysis are quite low, e.g., in the range of 0 to 3 meq/liter. These low concentrations of potassium are required for infrequent hemofiltration therapies, to prevent life threatening accumulations of serum potassium between treatment sessions. Interim accumulation of toxic levels of potassium can be encountered between infrequent hemofiltration sessions, both because of decreased renal excretion of potassium and the interim development of acidosis between sessions. This, in turn, can result in total body potassium depletion in many persons undergoing infrequent therapy. Potassium depletion results in vasoconstriction and subsequent alterations in regional blood flow. Potassium depletion also interferes with the efficiency of solute removal, as measured by a decrease in Kt/V for urea, which is a dimensionless parameter commonly employed to measure the adequacy of dialysis. Potassium depletion is also implicated in the pathogenesis of hypertension in patients undergoing hemodialysis or infrequent hemofiltration.

In contrast, the optimal range for potassium in a replacement fluid used for frequent hemofiltration can fall in a higher range than that required of less frequent treatment schedules, laying in the range of 2.7 to 4.5 meq/liter, and typically 4.0 meq/liter. This higher concentration of potassium, when infused frequently in smaller fluid replacement volumes, prevents potassium depletion, while also maintaining more stable potassium levels to prevent toxic accumulation of potassium between sessions.

Additional benefits derived from frequent hemofiltration in the control of serum potassium lay in the more physiologic control of acidosis, which prevents extra cellular shift of potassium from the intracellular space. In addition to the control of acidosis, the avoidance of total body potassium depletion enhances aldosterone-mediated gut elimination of potassium, further safeguarding against hyperkalemia.

The optimal range for chloride concentrations in a replacement fluid used for frequent hemofiltration is 105 to 115 meq/liter, and typically 109 meq/liter. This concentration most closely approximates the normal sodium to chloride ratio of 1.38:1 maintained in the plasma. The small deviation from this ratio in the replacement fluid itself allows for the normalization of the ratio by daily oral intake of these electrolytes. Due to the larger replacement fluid volumes needed for infrequent treatment (three times per week or less), this deviation from the normal 1.38:1 ratio are exaggerated, and can lead to a hyperchloremic acidosis. Due to the use of smaller fluid volumes during each frequent hemofiltration session, hyperchloremic acidosis can be avoided.

The optimal range of bicarbonate or an equivalent in a replacement fluid used for frequent hemofiltration is also important. Concentrations must adequately replace filtered bicarbonate while controlling acidosis and avoiding metabolic alkalosis. Because of precipitation of calcium carbonate in solutions containing dissolved calcium and bicarbonate, bicarbonate itself is generally impractical for use in a replacement fluid. Other substances such as acetate, citrate, or typically lactate, are substituted. These substances are metabolized by the body into bicarbonate and do not precipitate when placed into solution with the cationic substances mentioned previously.

The range of lactate necessary to replace filtered bicarbonate and control acidosis without alkalemia is 25 to 35 mmoles per liter, and typically 28 mmoles per liter. Due to the large volumes of replacement fluid used for infrequent therapies, use of lactate containing replacement fluids can result in lactate accumulation and pathologic alterations in the lactate:pyruvate ratio and resulting in undesirable changes in cellular redox potentials. However, these effects are minimized by the frequent use of smaller volumes of replacement fluid during frequent hemofiltration. This also results in more physiologic control of acidosis and, secondarily, serum potassium concentration. The latter is accounted for by reduced extra-cellular shift of potassium caused by acidosis.

The above observation also holds true for acetate and citrate, as well. The typical range of acetate in replacement fluid would be 25 to 35 mmoles/liter, and typically 30 mmoles/liter. The typical range of citrate would be 16 to 24 mmoles/liter, and typically 20 mmoles/liter. These concentrations render solutions containing acetate impractical for large volume replacements on an infrequent basis, because of toxicity incurred by the accumulation of acetate. These include both cardiac and hepatic toxicity. There are additional issues of calcium and magnesium chelation, which become significant when citrate is used in the large volumes necessary for infrequent therapy. These toxic effects attributable to acetate or citrate are minimized by the smaller replacement volumes required for daily hemofiltration.

The unique combination of electrolytes and basic substances discussed above represent a novel solution to the problem of choosing replacement fluid for frequent hemofiltration. The same constituents would not likely be applicable to less frequent treatment schedules.

Frequent hemofiltration minimizes the depletion of blood electrolytes during each hemofiltration session. Thus, the replacement fluid need not include replacement electrolytes. The source 252 may therefore supply relatively inexpensive commodity solutions of physiologic fluids, free of electrolytes, e.g., normal saline or Ringer's lactate (which typically contains 6 mg/ml sodium chloride (130 meq/liter); 3.1 mg/ml of sodium lactate (28 meq/liter); 0.3 mg/ml potassium chloride (4 meq/liter); 0.2 mg/ml calcium chloride (2.7 meq/liter, 109 meq/liter at an osmolarity of 272 mos/liter); at a pH of 6.0 to 7.5). When buffered with citrate, Ringer's lactate effectively achieves the fluid balancing function. The citrate used to buffer the inexpensive, electrolyte-free replacement fluid can also serve the additional function of anticoagulating the blood as it undergoes hemofiltration in the first place.

The source 252 supplying the ancillary materials 20 can comprise one or more companies or businesses that manufacture the ancillary materials or that otherwise distributes the ancillary materials 20 to the treatment location 12.

D. Exemplary Frequent Hemofiltration Modalities

The system 10 serves to enable frequent hemofiltration with high blood flow rates. The high blood flow rates reduce the processing time, and also significantly increases the transport rate of uremic toxins across the hemofiltration membrane. The frequent hemofiltration that the system 10 enables removes high concentrations of uremic toxins, without requiring the removal of high fluid volumes, with the attendant loss of electrolytes. The system 10 thereby provides multiple benefits for the individual, i.e., a tolerable procedure time (e.g., about one to two hours), with high clearance of uremic toxins, without high depletion of liquids and physiologic electrolyte levels in the blood, accurate fluid volume balancing, and use of inexpensive commodity replacement fluids.

The machine 16 and cartridge 18 that the system 10 may provide can be used to provide diverse frequent hemofiltration modalities on a continuous or extended basis, e.g., normal frequent hemofiltration, balanced frequent hemofiltration, only net ultrafiltration, and replacement fluid bolus.

During normal frequent hemofiltration, blood is drawn from the person at a prescribed flow rate (BFR). Waste fluid is removed from the arterial blood flow and volumetrically balanced with replacement fluid, which is returned in the venous blood flow at a prescribed rate (RFR). A prescribed net ultrafiltration volume of waste fluid is also removed at a prescribed flow rate (UFR) with fluid balancing, to control net weight loss. Operation of the machine 16 in the normal frequent hemofiltration mode terminates when either (i) the replacement fluid sensor indicates the absence of replacement fluid flow by sensing the presence of air (i.e., no more replacement fluid) and the net ultrafiltration goal has been achieved; or (ii) the time prescribed for the session has elapsed.

During balanced frequent hemofiltration, normal hemofiltration occurs without an ultrafiltration function. This mode can be used for persons that experience no weight gains between treatment sessions. This mode can also be used at the end of a normal frequent hemofiltration session, when the net ultrafiltration goal was achieved before exhausting the supply of replacement fluid.

During only net ultrafiltration, only a net ultrafiltration volume of waste is removed from the person. No fluid is replaced. This mode can be used when it is desired only to remove fluid. This mode can also be used at the end of a normal frequent hemofiltration session, when the net ultrafiltration goal has not been achieved but the supply of replacement fluid has been exhausted.

During replacement fluid bolus, there is no fluid balancing and ultrafiltration functions. Blood is circulated in an extracorpeal path and a bolus of replacement fluid is added. In the illustrated embodiment, the ultrafiltration pump 144 is run in reverse at a speed lower than the waste and replacement pump 152. This recirculates waste fluid through the waste compartments 212R and 214R, to add replacement fluid from the replacement compartments 212F and 214F to the patient. The waste fluid that is recirculated limits waste fluid removal through the hemofilter 34, yielding replacement fluid addition without additional waste fluid removal. The net volume of added replacement fluid conveyed to the patient equals the volume of waste fluid recirculated. This mode can be used to return fluid to a person in a bolus volume, e.g., during a hypotensive episode or during rinse back at the end of a given hemofiltration session.

1. Controlling the Blood Flow Rate

High blood flow rates (e.g., at least 300 ml/min, and preferably at least 600 ml/min) are conducive to rapid, efficient frequent hemofiltration. The high blood flow rates not only reduce the processing time, but also significantly increases the transport rate of uremic toxins across the hemofiltration membrane. In this way, the system 10 removes high concentrations of uremic toxins, without requiring the removal of high fluid volumes, with the attendant loss of electrolytes.

The BFR can be prescribed by an attending physician and input by the operator at the beginning of a treatment session. Alternatively, the machine 16 can automatically control to achieve an optimal BFR and minimize procedure time, based upon a desired filtration fraction value (FF), FPR, and UFR, as follows: BFR=(RFR+UFR)/FF.

where:

FF is the desired percentage of fluid to be removed from the blood stream through the hemofilter 34.

A desired FF (typically 20% to 35%) can be either preset or prescribed by the attending physician. A desired FF takes into account the desired therapeutic objectives of toxin removal, as well as the performance characteristics of the hemofilter 34. A nominal FF can be determined based upon empirical and observed information drawn from a population of individuals undergoing hemofiltration. A maximum value of 30% is believed to be appropriate for most individuals and hemofilters 34, to achieve a desired therapeutic result without clogging of the hemofilter 34.

In the illustrated embodiment, air leaks into the extracorpbreal circuit (due, e.g., to improper patient line connection) is monitored by the sensor 98. The sensor 98 is an ultrasonic detector, which also can provide the added capacity to sense flow rate.

In the illustrated embodiment, the machine 16 senses waste fluid pressure to control the blood flow rate to optimize the removal of fluid across the hemofilter 34. As arterial blood flows through the hemofilter 34 (controlled by the blood pump 92), a certain volume of waste fluid will cross the membrane into the waste line 118. The volume of waste fluid entering the waste line 118 depends upon the magnitude of the waste fluid pressure, which is sensed by the sensor 132. The waste fluid pressure is adjusted by controlling the waste fluid removal rate through the fluid balancing compartments (i.e., through control of the waste and replacement pump 152).

The machine 16 monitors the waste fluid pressure at sensor 132. By keeping the pressure sensed by the sensor 132 slightly above zero, the machine 16 achieves the maximum removal of fluid from the blood at then operative arterial flow rate. Waste pressure values significantly higher than zero will limit removal of fluid from the blood and keep a higher percentage of waste fluid in the blood (i.e., result in a lower filtration fraction). However, this may be desirable for persons who tend to clot easier.

By sensing waste fluid pressure by sensor 132, the machine 16 also indirectly monitors arterial blood pressure. At a constant blood pump speed, changes in arterial blood flow caused, e.g., by access clotting or increased arterial blood pressure, makes less waste fluid available in the waste line 118. At a given speed for pump 152, change in arterial blood flow will lower the sensed waste pressure at sensor 132 to a negative value, as fluid is now drawn across the membrane. The machine 16 adjusts for the change in arterial blood flow by correcting the waste fluid removal rate through the pump 152, to bring the waste pressure back to slightly above zero, or to another set value.

In this arrangement, a pressure sensor in the arterial blood line is not required. If the arterial pressure increases at a fixed blood pump speed, the blood flow must drop, which will result in a sensed related drop in the waste fluid pressure by the sensor 132. Adjusting the pump 152 to achieve a pressure slightly above zero corrects the reduced arterial blood flow. In this arrangement, since the waste fluid pressure is maintained at a slightly positive value, it is not possible to develop a reverse transmembrane pressure, which conveys waste fluid back to the person's blood. The maximum transmembrane pressure is the maximum venous pressure, since waste fluid pressure is held slightly positive.

In an alternative arrangement, arterial blood pressure can be measured by a sensor located upstream of the blood pump. The rate of the blood pump is set to maintain sensed arterial blood pressure at a predetermined control point. This controls the blood pump speed to a maximum rate. The control point can be determined by the attending physician, e.g., on a day-to-day basis, to take into account the blood access function of the person undergoing treatment. Use of an arterial pressure control point minimizes the treatment time, or, alternatively, if treatment time is fixed, the removal of waste fluid can maximized.

In this arrangement, safety alarms can be included should the sensed arterial pressure become more negative than the control point, along with a function to shut down the blood pump should an alarm occur.

2. Controlling the Replacement Fluid Flow Rate

RFR can be prescribed by an attending physician and inputted by the operator at the beginning of a treatment session.

Alternatively, the machine 16 can automatically control RFR to minimize procedure time based upon the desired filtration fraction value (FF), BFR, and UFR, as follows: RFR=(BFR*FF)−UFR.

In the illustrated embodiment, waste is conveyed to the waste side compartments 212R and 214R, and replacement fluid is conveyed to the replacement side compartments 212F and 214F, by operation of the dual header waste and replacement fluid pump 152. Alternatively, separate waste and replacement fluid pumps can be provided.

The speed of the waste and replacement pump 152 is controlled to achieve the desired RFR. The machine 16 cycles the inlet and outlet valve assemblies 216, 218, as described. The machine 16 cycles between the valve states according to the speed of the waste and fluid pump 152 to avoid overfilling the compartments 212, 214 receiving fluid. Various synchronization techniques can be used.

In one arrangement, as previously described, the interval of a valve cycle is timed according to the RFR, so that the volume of waste or replacement fluid supplied to waste compartment during the valve cycle interval is less than volume of the compartment receiving the waste fluid. Overfilling is thereby avoided without active end of cycle monitoring. In a preferred embodiment, the waste fluid is pumped at RFR, and the replacement fluid is pumped at a higher rate, but is subject to pressure relief through the pressure relief path 240 upon filling the corresponding replacement side compartment 214.

In another arrangement, the timing of the transition between valve cycles is determined by active sensing of pressure within the compartments 212, 214 receiving liquid. As the interior wall 210 reaches the end of its travel, pressure will increase, signaling an end of cycle to switch valve states.

In yet another arrangement, the location of the interior wall 210 as it reaches the end of its travel is actively sensed by end of cycle sensors on the machine 16. The sensors can comprise, e.g., optical sensors, capacitance sensors, magnetic Hall effect sensors, or by radio frequency (e.g., microwave) sensors. The termination of movement of the interior wall 210 indicates the complete filling of a compartment and the concomitant emptying of the other compartment, marking the end of a cycle. The sensors trigger an end of cycle signal to switch valve states.

The machine 16 counts the valve cycles. Since a known volume of replacement fluid is expelled from a replacement side compartment during each valve cycle, the machine 16 can derive the total replacement volume from the number of valve cycles. The replacement fluid volume is also known by the number of replacement fluid bags of known volume that are emptied during a given session.

Frequent hemofiltration can be conducted without fluid replacement, i.e., only net ultrafiltration, by setting RFR to zero.

3. Controlling the Ultrafiltration Flow Rate

UFR can be prescribed by an attending physician and inputted by the operator at the beginning of a treatment session.

The speed of the ultrafiltration pump is monitored and varied to maintain UFR.

Frequent hemofiltration can be conducted without an ultrafiltration function, i.e., balanced hemofiltration, by setting UFR to zero.

4. Active Filtration Rate Control

In an alternative embodiment, the machine 16 also actively controls the filtration rate along with the blood flow rate, to achieve a desired magnitude of uremic toxin removal through the hemofilter 34.

In this embodiment, the machine 16 includes a flow restrictor which is positioned to engage a region of the venous blood return path in the circuit 56. The restrictor comprises, e.g., a stepper-driven pressure clamp, which variably pinches a region of the venous blood return path upon command to alter the outlet flow rate of blood. This, in turn, increases or decreases the transmembrane pressure across the filter membrane.

For a given blood flow rate, waste transport across the filter membrane will increase with increasing transmembrane pressure, and vice versa. However, at some point, an increase in transmembrane pressure, aimed at maximizing waste transport across the filter membrane, will drive cellular blood components against the filter membrane. Contact with cellular blood components can also clog the filter membrane pores, which decreases waste transport through the membrane.

Filtration rate control can also rely upon an upstream sensor mounted on the machine 16. The sensor is positioned for association with a region of the arterial blood supply path between the blood pump 92 and the inlet of the hemofilter 34. The sensor senses the hematocrit of the blood prior to its passage through the filter membrane which will be called the "pre-treatment hematocrit"). In the arrangement, a downstream sensor is also mounted on the machine 16. The sensor is positioned for associated with a region of the venous blood return path downstream of the outlet of the hemofilter 34. The sensor senses the hematocrit of the blood after its passage through the hemofilter 34(which will be called the "post-treatment hematocrit").

The difference between pre-treatment and post-treatment hematocrit is a function of the degree of waste fluid removal by the hemofilter 34. That is, for a given blood flow rate, the more waste fluid that is removed by the hemofilter 34, the greater the difference will be between the pre-treatment and post-treatment hematocrits, and vice versa. The machine 16 can therefore derive an actual blood fluid reduction ratio based upon the difference detected by sensors between the pre-treatment and post-treatment hematocrits. The machine 16 periodically compares the derived fluid reduction value, based upon hematocrit sensing by the sensors, with the desired FF. The machine 16 issues a command to the flow restrictor to bring the difference to zero.

5. Set Up Pressure Testing/Priming

Upon mounting the disposable fluid circuit on the machine 16, the pumps can be operated in forward and reverse modes and the valves operated accordingly to establish predetermined pressure conditions within the circuit. The sensors monitor build up of pressure within the circuit, as well as decay in pressure over time. In this way, the machine can verify the function and integrity of pumps, the pressure sensors, the valves, and the flow paths overall.

The machine 16 can also verify the accuracy of the ultrafiltration pump using the fluid balancing containers.

Priming can be accomplished at the outset of each frequent hemofiltration session to flush air and any residual fluid from the disposable fluid circuit. Fluid paths from the arterial access to the waste bag are flushed with replacement fluid. Replacement fluid is also circulated through the fluid balancing containers into the waste bag and the venous return path. The higher flow rate in the replacement fluid path and timing of the fluid balancing valve elements assure that the replacement fluid compartments completely fill and the waste fluid compartments completely empty during each cycle for priming.

6. Rinse Back

As previously described, waste fluid pressure is controlled and monitored to assure its value is always positive. Likewise, pressure between the blood pump and the hemofilter must also be positive, so that air does not enter this region of the circuit. Forward operation of the blood pump to convey arterial blood into the hemofilter establishes this positive pressure condition.

The rinse back of blood at the end of a given frequent hemofiltration procedure can also be accomplished without risk of air entry into the blood flow path. Rinse can be accomplished by stopping the blood pump and operating the ultrafiltration pump in the reverse bolus mode, as already described. The recirculation of waste fluid by the ultrafiltration pump through the fluid balancing compartments introduces replacement fluid to flush the venous return line. When complete, the venous clamp is closed.

With the venous clamp closed, continued operation of the ultrafiltration pump in the reverse bolus mode introduces replacement fluid from the fluid balancing compartments into the hemofilter, in a back flow direction through the outlet port. The blood pump is run in reverse to convey the replacement fluid through the hemofilter and into the arterial blood line. Residual blood is flushed from the blood line. The blood pump is operated in reverse at a rate slower than the reverse bolus rate of the ultrafiltration pump (which supplies replacement fluid to the outlet port of the hemofilter), so that air cannot enter the blood path between the blood pump and the hemofilter. At this stage of the rinse back, the arterial blood line is also subject to positive pressure between the blood pump and the arterial access, so no air can enter this region, either.

In this arrangement, no air sensing is required in the arterial blood line and a pressure sensor between the blood pump and the hemofilter is required.

E. Supplying Telemetry

Figure 19:
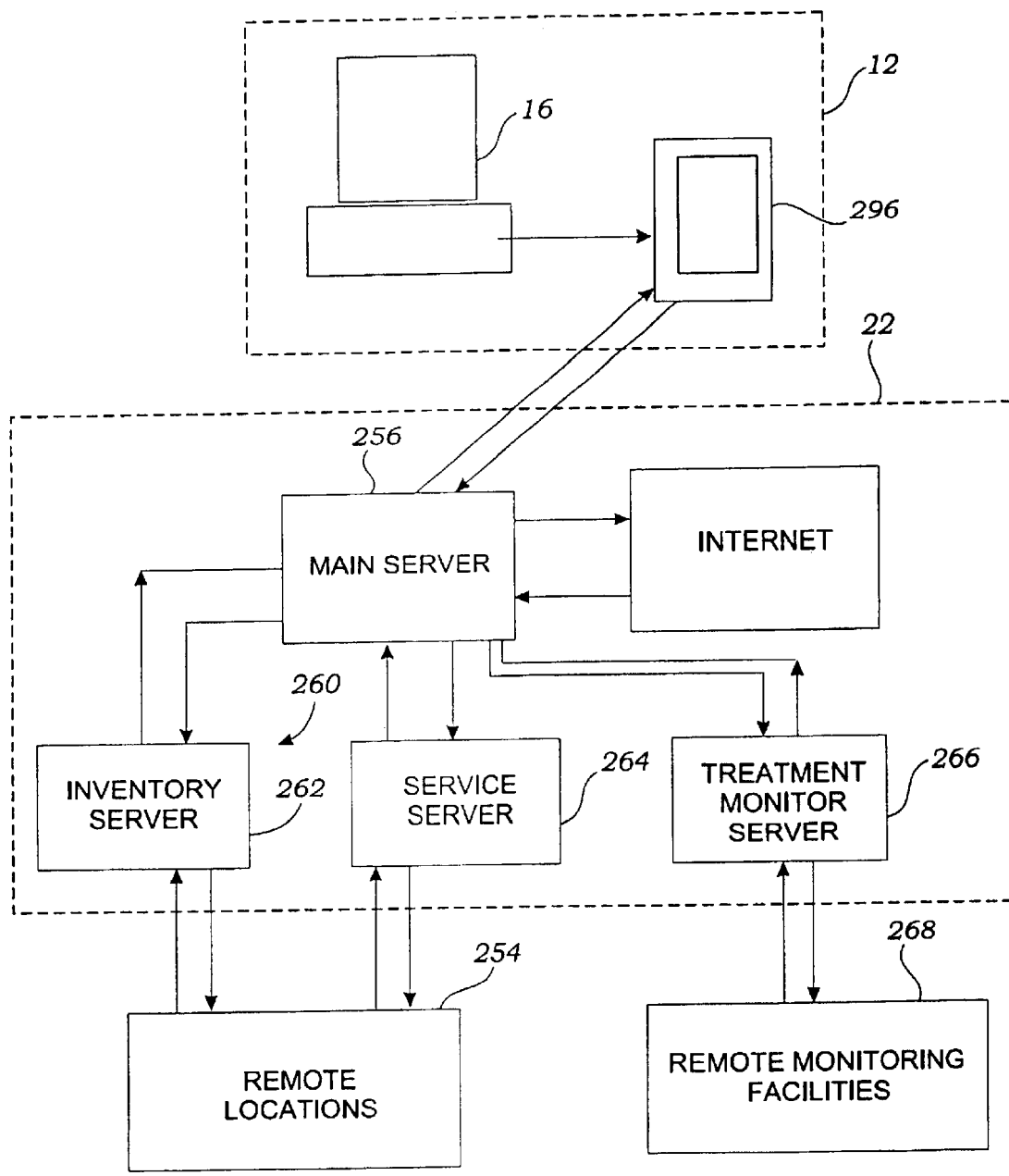
FIG. 19 is a diagrammatic view of a telemetry network that can form a part of the system shown in FIG. 1.

The system 10 also preferably includes a telemetry network 22 (see FIGS. 1 and 19). The telemetry network 22 provides the means to link the machine 16 at the treatment location 12 in communication with one or more remote locations 254 via, e.g., cellular networks, digital networks, modem, Internet, or satellites. A given remote location 254 can, for example, receive data from the machine 16 at the treatment location 12 or transmit data to a data transmission/receiving device 296 at the treatment location 12, or both. A main server 256 can monitor operation of the machine 16 or therapeutic parameters of the person undergoing frequent hemofiltration. The main server 256 can also provide helpful information to the person undergoing frequent hemofiltration. The telemetry network 22 can download processing or service commands to the data receiver/transmitter 296 at the treatment location 12.

Further details about the telemetry aspect of the system 10 will now be described.

1. Remote Information Management

FIG. 19 shows the telemetry network 22 in association with a machine 16 that carries out frequent hemofiltration. The telemetry network 22 includes the data receiver/transmitter 296 coupled to the machine 16. The data receiver/transmitter 296 can be electrically isolated from the machine 16, if desired. The telemetry network 22 also includes a main data base server 256 coupled to the data receiver/transmitter 296 and an array of satellite servers 260 linked to the main data base server 256.

The data generated by the machine 16 during operation is processed by the data receiver/transmitter 296. The data is stored, organized, and formatted for transmission to the main data base server 256. The data base server 256 further processes and dispenses the information to the satellite data base servers 260, following by pre-programmed rules, defined by job function or use of the information. Data processing to suit the particular needs of the telemetry network 22 can be developed and modified without changing the machine 16.

The main data base server 256 can be located, e.g., at the company that creates or manages the system 10.

The satellite data base servers 260 can be located, for example, at the residence of a designated remote care giver for the person, or at a full time remote centralized monitoring facility staffed by medically trained personnel, or at a remote service provider for the machine 16, or at a company that supplies the machine 16, or the processing cartridge 18, or the ancillary processing material to the treatment location 12.

Linked to the telemetry network 22, the machine 16 acts as a satellite. The machine 16 performs specified therapy tasks while monitoring basic safety functions and providing the person at the treatment location 12 notice of safety alarm conditions for resolution. Otherwise, the machine 16 transmits procedure data to the telemetry network 22. The telemetry network 22 relieves the machine 16 from major data processing tasks and related complexity. It is the main data base server 256, remote from the machine 16, that controls the processing and distribution of the data among the telemetry network 22, including the flow of information and data to the person undergoing therapy. The person at the treatment location 12 can access data from the machine 16 through the local date receiver/transmitter 296, which can comprise a laptop computer, handheld PC device, web tablet, or cell phone.

The machine 16 can transmit data to the receiver/transmitter 296 in various ways, e.g., electrically, by phone lines, optical cable connection, infrared light, or radio frequency, using cordless phone/modem, cellular phone/modem, or cellular satellite phone/modem. The telemetry network 22 may comprise a local, stand-alone network, or be part of the Internet.

For example, when the machine 16 notifies the person at the treatment location 12 of a safety alarm condition, the safety alarm and its underlying data will also be sent to the main server 256 on the telemetry network 22 via the receiver/transmitter 296. While the person undergoing therapy or the care giver works to resolve the alarm condition, the main server 256 determines, based upon the prevailing data rule, whether the alarm condition is to be forwarded to other servers 260 in the network 22.

When an alarm condition is received by the main server 256, the main server 256 can locate and download to the receiving device 296 the portion of the operator's manual for the machine that pertains to the alarm condition. Based upon this information, and exercising judgment, the operator/user can intervene with operation of the machine 16. In this way, the main server 256 can provide an automatic, context-sensitive help function to the treatment location 12. The telemetry network 22 obviates the need to provide on-board context-sensitive help programs for each machine 16. The telemetry network 22 centralizes this help function at a single location, i.e., a main server 256 coupled to all machines 16.

The telemetry network 22 can relay to an inventory server 262 supply and usage information of components used for frequent hemofiltration at each treatment location 12. The server 262 can maintain treatment site-specific inventories of such items, such as cartridges 18, replacement fluid, and hemofilters 34. The company or companies of the system 10 that supply the machine 16, or the processing cartridge 18, or the ancillary processing material to the treatment location 12 can all be readily linked through the telemetry network 22 to the inventory server 262. The inventory server 262 thereby centralizes inventory control and planning for the entire system 10, based upon information received in real time from each machine 16 at each treatment location 12.

The telemetry network 22 can relay to a service server 264 hardware status information for each machine 16 at every treatment location 12. The service server 264 can process the information according to preprogrammed rules, to generate diagostic reports, service requests or maintenance schedules. The company or companies of the system 10 that supply or service the machine 16 can all be readily linked through the telemetry network 22 to the service server 264. The service server 264 thereby centralizes service, diagnostic, and maintenance functions for the entire system 10. Service-related information can also be sent to the treatment location 12 via the receiving device 296.

The telemetry network 22 can also relay to a treatment monitoring server 266, treatment-specific information pertaining to the hemofiltration therapy provided by each machine 16 for the person at each treatment location 12. Remote monitoring facilities 268, staffed by medically trained personnel, can be readily linked through the telemetry network 22 to the treatment monitoring server 266. The monitoring server 266 thereby centralizes treatment monitoring functions for all treatment locations 12 served by the system 10. Treatment-monitoring information can also be sent to the treatment location 12 via the receiving device 296.

The telemetry network 22 can also provide through the device 296 an access portal for the person undergoing frequent hemofiltration to the myriad services and information contained on the Internet, e.g., over the web radio and TV, video, telephone, games, financial management, tax services, grocery ordering, prescriptions purchases, etc. The main server 256 can compile diagnostic, therapeutic, and/or medical information to create a profile for each person served by the system 10 to develop customized content for that person. The main server 256 thus provide customized ancillary services such as on line training, billing, coaching, mentoring, and provide a virtual community whereby persons using the system 10 can contact and communicate via the telemetry network 22.

The telemetry network 22 thus provides the unique ability to remotely monitor equipment status, via the internet, then provide information to the user, also via the internet, at the location of the equipment. This information can includes, e.g., what page on the operator's manual would be the most helpful for their current operational situation, actual data about the equipment's performance (e.g., could it use service, or is it set up based on the caretaker's recommendations, data about the current session i.e., buttons pressed, alarms, internal machine parameters, commands, measurements.

The remote site can monitor the equipment for the same reasons that the user might. It can also retrieve information about the machine when it is turned off because the telemetry device is self-powered. It retains all information about the machine over a period of time (much like a flight recorder for an airplane).

2. On Site Programming (i) Using the Telemetry Network

The main server 256 on the telemetry network 22 can also store and download to each machine 16 (via the device 296) the system control logic and programs necessary to perform a desired frequent hemofiltration procedure. Programming to alter a treatment protocol to suit the particular needs of a single person at a treatments site can be developed and modified without a service call to change the machine 16 at any treatment location 12, as is the current practice. System wide modifications and revisions to control logic and programs that condition a machine 16 to perform frequent hemofiltration can be developed and implemented without the need to retrofit each machine 16 at all treatment locations 12 by a service call. This approach separates the imparting of control functions that are tailored to particular procedures, which can be downloaded to the machine 16 at time of use, from imparting safety functions that are generic to all procedures, which can be integrated in the machine 16.

(ii) Using the Cartridge

Alternatively, the control logic and programs necessary to perform a desired frequent hemofiltration procedure can be carried in a machine readable format on the cartridge 18. Scanners on the machine 16 automatically transfer the control logic and programs to the machine 16 in the act of loading the cartridge 18 on the machine 16. Bar code can be used for this purpose. Touch contact or radio frequency silicon memory devices can also be used. The machine 16 can also include local memory, e.g., flash memory, to download and retain the code.

For example, as FIG. 2 shows, the machine 16 can include one or more code readers 270 on the chassis panel 26. The tray 48 carries, e.g., on a label or labels, a machine readable (e.g., digital) code 272 (see FIG. 10) that contains the control logic and programs necessary to perform a desired frequent hemofiltration procedure using the cartridge 18. Loading the tray 48 on the machine 16 orients the code 272 to be scanned by the reader(s) 270. Scanning the code 272 downloads the control logic and programs to memory. The machine 16 is thereby programmed on site.

The code 272 can also include the control logic and programs necessary to monitor use of the the cartridge 18. For example, the code 272 can provide unique identification for each cartridge 18. The machine 16 registers the unique identification at the time it scans the code 272. The machine 16 transmits this cartridge 18 identification information to the main server 256 of the telemetry network 22. The telemetry network 22 is able to uniquely track cartridge 18 use by the identification code throughout the system 10.

Furthermore, the main server 256 can include preprogrammed rules that prohibit multiple use of a cartridge 18, or that limit extended uses to a prescribed period of time. An attempted extended use of the same cartridge 18 on any machine 16, or an attempted use beyond the prescribed time period, will be detected by the machine 16 or the main server 256. In this arrangement, the machine 16 is disabled until an unused cartridge 18 is loaded on the machine 16.

Service cartridges can also be provided for the machine 16. A service cartridge carries a code that, when scanned by the reader or readers on the chassis panel 26 and downloaded to memory, programs the machine 16 to conduct a prescribed service and diagnostic protocol using the service cartridge 18.

(iii) Using an Overlay

Figure 20:
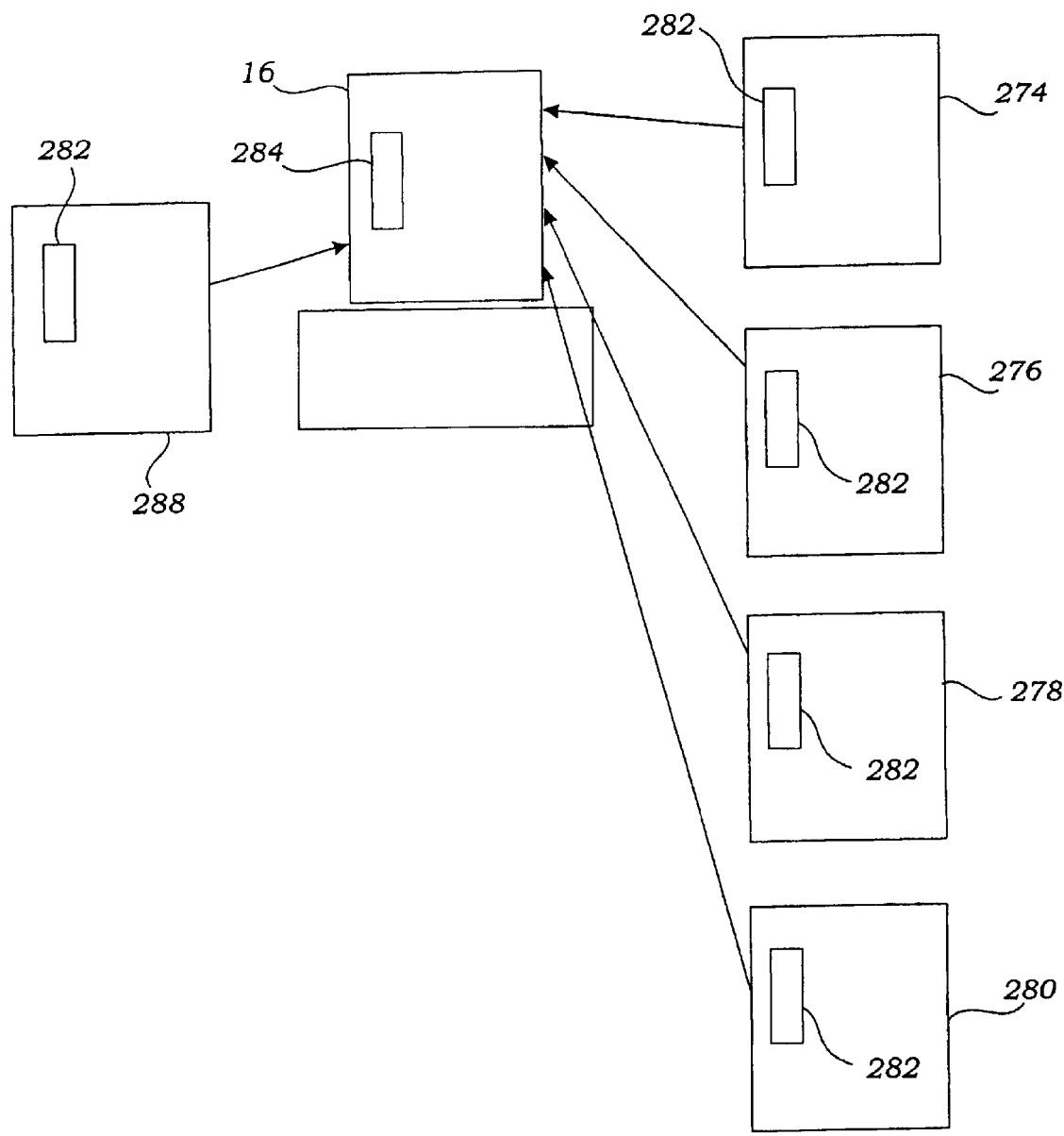
FIG. 20 is a diagrammatic view of overlays for imparting control logic to the machine shown in FIG. 2.

Alternatively, or in combination with any of the foregoing on-site machine 16 programming techniques, the chassis panel 26 can be configured to receive overlays 274, 276, 278, 280 (see FIG. 20), which are specific to particular hemofiltration modalities or therapies that the machine 16 can carry out. For example, in the context of the illustrated embodiment, one overlay 274 would be specific to the normal frequent hemofiltration mode, a second overlay 276 would be specific to the balanced frequent hemofiltration mode, a third overlay 278 would be specific to the only net ultrafiltration mode, and a fourth overlay 280 would be specific to the replacement fluid bolus mode. Other overlays could be provided, e.g., for a pediatric hemofiltration procedure, or a neo-natal hemofiltration procedure.

When a treatment location 12 wants to conduct a particular hemofiltration modality, the treatment location 12 mounts the associated overlay on the chassis panel 26. Each overlay contains a code 282 or a chip imbedded in the overlay that is scanned or discerned by one or more readers 284 on the chassis panel 26 after the overlay is mounted on the chassis panel 26. The code 282 is downloaded to flash memory on the machine 16 and programs the machine 16 to conduct hemofiltration in that particular mode.

A person at the treatment location 12 mounts the appropriate overlay 274, 276, 278, 280 and then mounts a cartridge 18 on the chassis panel 26. The machine 16 is then conditioned by the overlay and made capable by the cartridge 18 to conduct that particular mode of hemofiltration using the cartridge 18. In this way, a universal cartridge 18, capable of performing several hemofiltration modes, can be provided. It is the overlay that conditions the machine 16 to perform different treatment modalities. Alternatively, the operator can link the overlay, machine, and cartridge together by therapy type.

Furthermore, treatment-site specific alterations of generic hemofiltration modes can be developed and implemented. In this arrangement, treatment-site specific overlays 286 are provided for the machine 16. The treatment site-specific overlay 286 carries a code 282 or a chip imbedded in the overlay that, when downloaded by the machine 16, implements a particular variation of the hemofiltration mode for the person at that treatment location 12, as developed, e.g., by an attending physician. A person at the treatment location 12 mounts the treatment-site specific overlay 286 and then mounts a universal cartridge 18 on the chassis panel 26. The machine 16 is conditioned by the treatment site-specific overlay 286 and made capable by the universal cartridge 18 to conduct that particular specific mode of hemofiltration using the cartridge 18.

An additional overlay 288 can be provided that contains code 282 or a chip imbedded in the overlay that, when scanned by the reader(s) 284 on the chassis panel 26 and downloaded to flash memory, programs the machine 16 to conduct a prescribed service and diagnostic protocol using the cartridge 18, which is also mounted on the chassis panel 26.

F. Extended Use of the Cartridge

The consolidation of all blood and fluid flow paths in a single, easily installed cartridge 18 avoids the potential of contamination, by minmizing the number of connections and disconnections needed during a hemofiltration session. By enabling a dwell or wait mode on the machine 16, the cartridge 18 can remain mounted to the machine 16 after one hemofiltration session for an extended dwell or break period and allow reconnection and continued use by the same person in a subsequent session or in a continuation of a session following x-rays or testing.

The cartridge 18 can therefore provide multiple intermittent treatment sessions during a prescribed time period, without exchange of the cartridge 18 after each treatment session. The time of use confines are typically prescribed by the attending physician or technical staff for the treatment center to avoid biocontamination and can range, e.g., from 48 hours to 120 hours, and more typically 72 to 80 hours. The cartridge 18 can carry a bacteriostatic agent that can be returned to the patient (e.g., an anticoagulant, saline, ringers lactate, or alcohol) and/or be refrigerated during storage.

Figure 21:
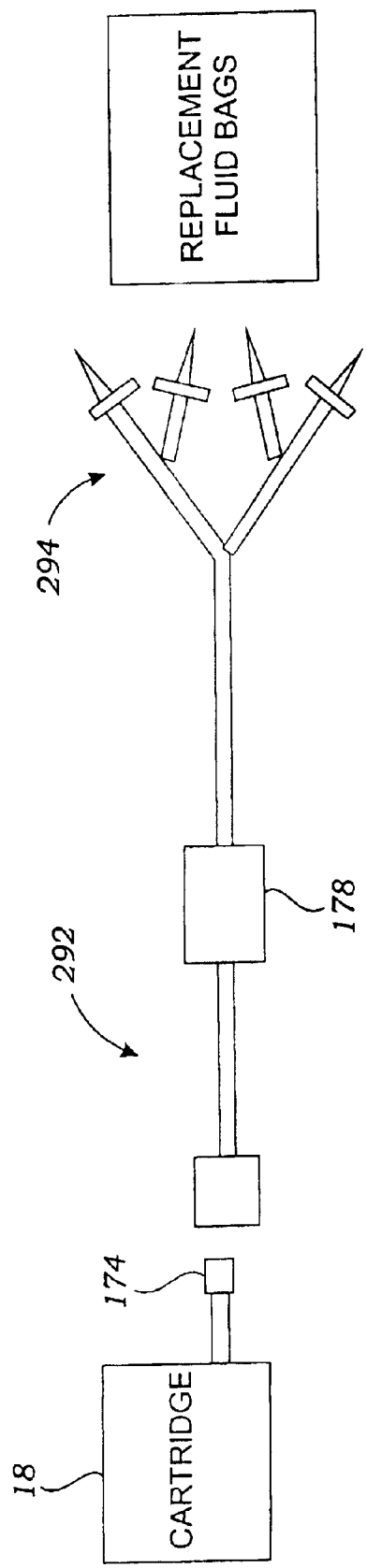
FIG. 21 is an embodiment of a set for attaching multiple replacement fluid bags to the cartridge shown in FIG. 10, the set including an in-line sterilizing filter.

To reduce the change of biocontamination, the cartridge 18 can include one or more in-line sterilizing filters 178 (e.g., 0.2 m) in association with connectors that, in use, are attached to outside fluid sources, e.g., the replacement fluid source. As FIG. 11 shows, the filter 178 can be pre-attached to the cartridge 18 and be coupled to a multiple connection set 290, which itself is coupled to the prescribed number of replacement fluid bags 176. Alternative (as FIG. 21 shows), a separate customized filtration set 292 can be provided, which attaches to the connector 174 carried by the cartridge 18. The filtration set 292 includes a sterilizing filter 178 to which an array of multiple connector leads 294 is integrated.

In the dwell mode of the machine 16, fluid can be recirculated either continuously or intermittently through the circuit 56. The fluid can be circulate past a region of ultraviolet light carried on the machine 16 to provide a bacteriostatic effect. Alternatively, or in combination with exposure to ultraviolet light, the fluid can carry a bacteriostatic agent, such as an anticoagulant, saline, ringers lactate, or alcohol, which can be returned to the person at the beginning of the next treatment session. The machine 16 and cartridge 18 can also be subjected to refrigeration during the dwell period.

In an alternative embodiment, an active disinfecting agent can be circulated through the circuit 56 during the dwell period. The disinfecting material can include a solution containing Amuchinaj material. This material can be de-activated by exposure to ultraviolet light prior to the next treatment session. Exposure to ultraviolet light causes a chemical reaction, during which AmuchinaJ material breaks down and transforms into a normal saline solution, which can be returned to the person at the start of the next hemofiltration session.

G. The Operator Interface

Figure 22:
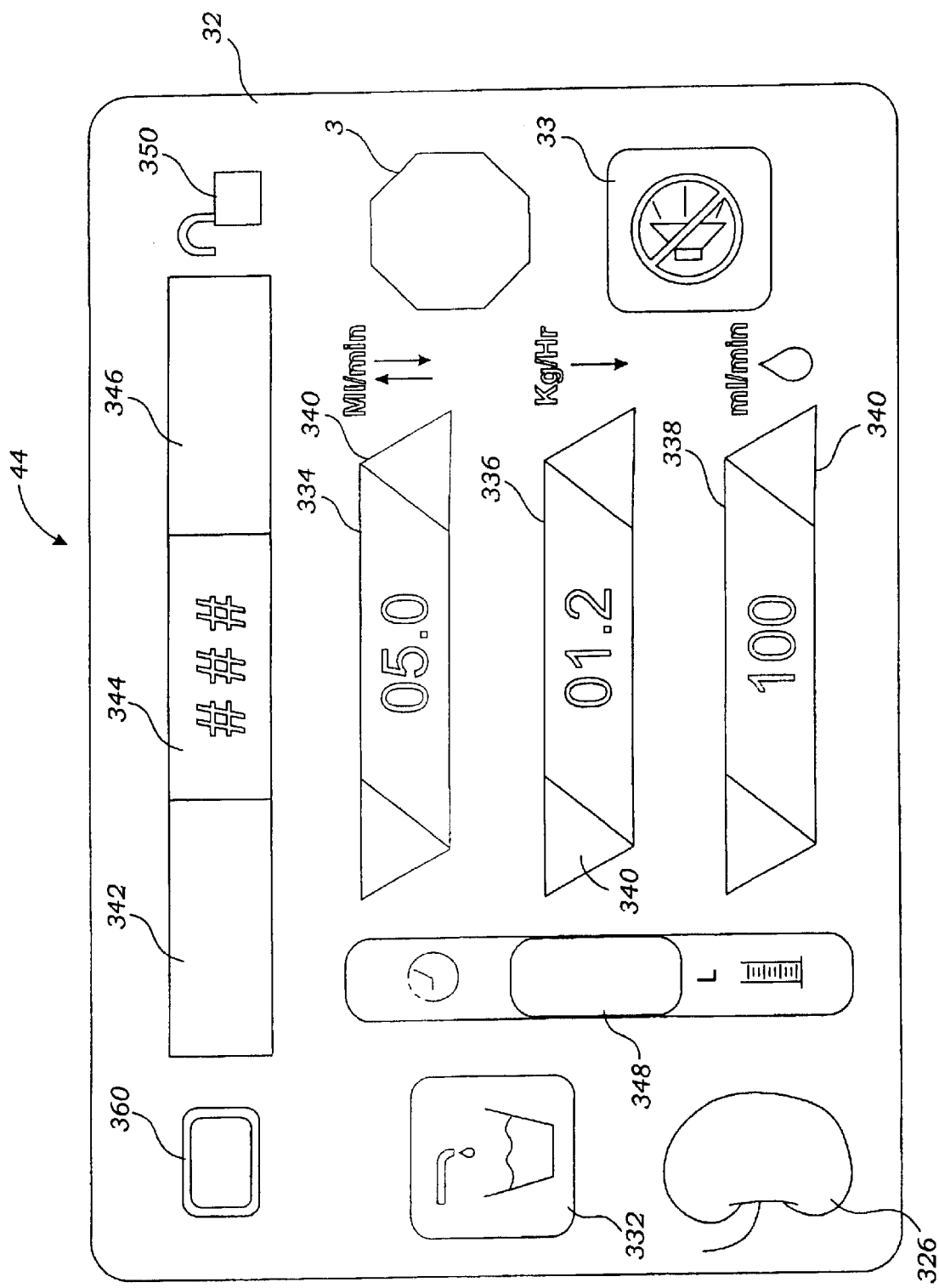
FIG. 22 is a plane view of a graphical user interface that the hemofiltration machine shown in FIG. 2 can incorporate.

FIG. 22 shows a representative display 324 for an operator interface 44 for the machine. The display 324 comprises a graphical user interface (GUI), which, in the illustrated embodiment, is displayed by the interface 44 on the exterior of the door 28, as FIG. 2 shows. The GUI can be realized, e.g., as a membrane switch panel, using an icon-based touch button membrane. The GUI can also be realized as a "C" language program implemented using the MS WINDOWS™ application and the standard WINDOWS 32 API controls, e.g., as provided by the WINDOWS™ Development Kit, along with conventional graphics software disclosed in public literature.

The GUI 324 presents to the operator a simplified information input and output platform, with graphical icons, push buttons, and display bars. The icons, push buttons, and display bars are preferably back-lighted in a purposeful sequence to intuitively lead the operator through set up, execution, and completion of a frequent hemofiltration session.

The GUI 324 includes an array of icon-based touch button controls 326, 328, 330, and 332. The controls include an icon-based treatment start/select touch button 326, an icon-based treatment stop touch button 328, and an icon-based audio alarm mute touch button 330. The controls also include an icon-based add fluid touch button 332 (for prime, rinse back, and bolus modes, earlier described).

An array of three numeric entry and-display fields appear between the icon-based touch buttons. The fields comprise information display bars 334, 336, and 338, each with associated touch keys 340 to incrementally change the displayed information. In the illustrated embodiment, the top data display bar 334 numerically displays the Replacement Fluid Flow Rate (in ml/min), which is the flow rate for removing waste fluid and replacing it with an equal volume of replacement fluid. The middle data display bar 336 numerically displays the ultrafiltration flow rate (in kg/hr), which is the flow rate for removing waste fluid to control net weight loss. The bottom data display bar 338 numerically displays the Blood Pump Flow Rate (in ml/min).

The associated touch keys 340 point up (to increase the displayed value) or down (to decrease the displayed value), to intuitively indicate their function. The display bars 334, 336, and 338 and touch keys 340 can be shaded in different colors, e.g., dark blue for the replacement flow rate, light blue for ultrafiltrational flow rate, and red for the blood flow rate.

An array of status indicator bars appears across the top-of the screen. The left bar 342, when lighted, displays a "safe" color (e.g., green) to indicate a safe operation condition. The middle bar 344, when lighted, displays a "cautionary" color (e.g., yellow) to indicate a caution or warning condition and may, if desired, display a numeric or letter identifying the condition.

The right bar 346, when lighted, displays an "alarm" color (e.g., red) to indicate a safety alarm condition and may, if desired, display a numeric or letter identifying the condition.

Also present on the display is a processing status touch button 348. The button 348, when touched, changes for a period of time (e.g., 5 seconds) the values displayed in the information display bars 334, 336, and 338, to show the corresponding current real time values of the replacement fluid volume exchanged (in the top display bar 334), the ultrafiltrate volume (in the middle display bar 336), and the blood volume processed (in the bottom display bar 338). The status button 348, when touched, also shows the elapsed procedure time in the left status indicator bar 342.

The display also includes a cartridge status icon 350. The icon 350, when lighted, indicates that the cartridge 18 can be installed or removed from the machine 16.

The GUI 324, though straightforward and simplified, enables the operator to set the processing parameters for a given treatment session in different ways.

For example, in one input mode, the GUI 324 prompts the operator by back-lighting the replacement fluid display bar 334, the ultrafiltration display bar 336, and the blood flow rate display bar 338. The operator follows the lights and enters the desired processing values using the associated touch up/down bottons 340. The GUI backlights the start/select touch button 326, prompting the operator to begin the treatment. In this mode, the machine 16 controls the pumps to achieve the desired replacement fluid, ultrafiltration, and blood flow rates set by the operator. The machine terminates the procedure when all the replacement fluid is used and the net ultrafiltration goal is achieved.

In another input mode, the operator can specify individual processing objectives, and the machine 16 will automatically set and maintain appropriate pump values to achieve these objectives. This mode can be activated, e.g., by pressing the start/select touch button 326 while powering on the machine 16. The GUI 324 changes the function of the display bars 334 and 336, so that the operator can select and change processing parameters. In the illustrated embodiment, the processing parameters are assigned identification numbers, which can be scrolled through and selected for display in the top bar 334 using the touch up/down keys 340. The current value for the selected parameter is displayed in the middle display bar 336, which the operator can change using the touch up/down keys 340.

In this way, the operator can, e.g., specify a desired filtration factor value (FF) along with a desired ultrafiltration flow rate (UFR) and replacement fluid flow rate (RFR). The machine will automatically control the blood pump rate (BFR), based upon the relationship BFR=(RFR+UFR)/FF, as previously described.

Alternatively, the operator can specify a desired filtration factor value (FF) along with a desired ultrafiltration flow rate (UFR) and blood flow rate (BFR). The machine will automatically control the replacement fluid pump rate (RFR), based upon the relationship RFR=(BFR*FF)–UFR, as already described.

Alternatively, the operator can specify only an ultrafiltration volume. In this arrangement, the machine 16 senses waste fluid pressure to automatically control the blood flow rate to optimize the removal of fluid across the hemofilter 34, as previously described. Alternatively, the machine can automatically control the blood flow rate to optimize removal of fluid based a set control arterial blood pressure, as also already described.

As FIG. 22 shows, the interface also preferably includes an infrared port 360 to support the telemetry function, as previously described.

Figure 23:
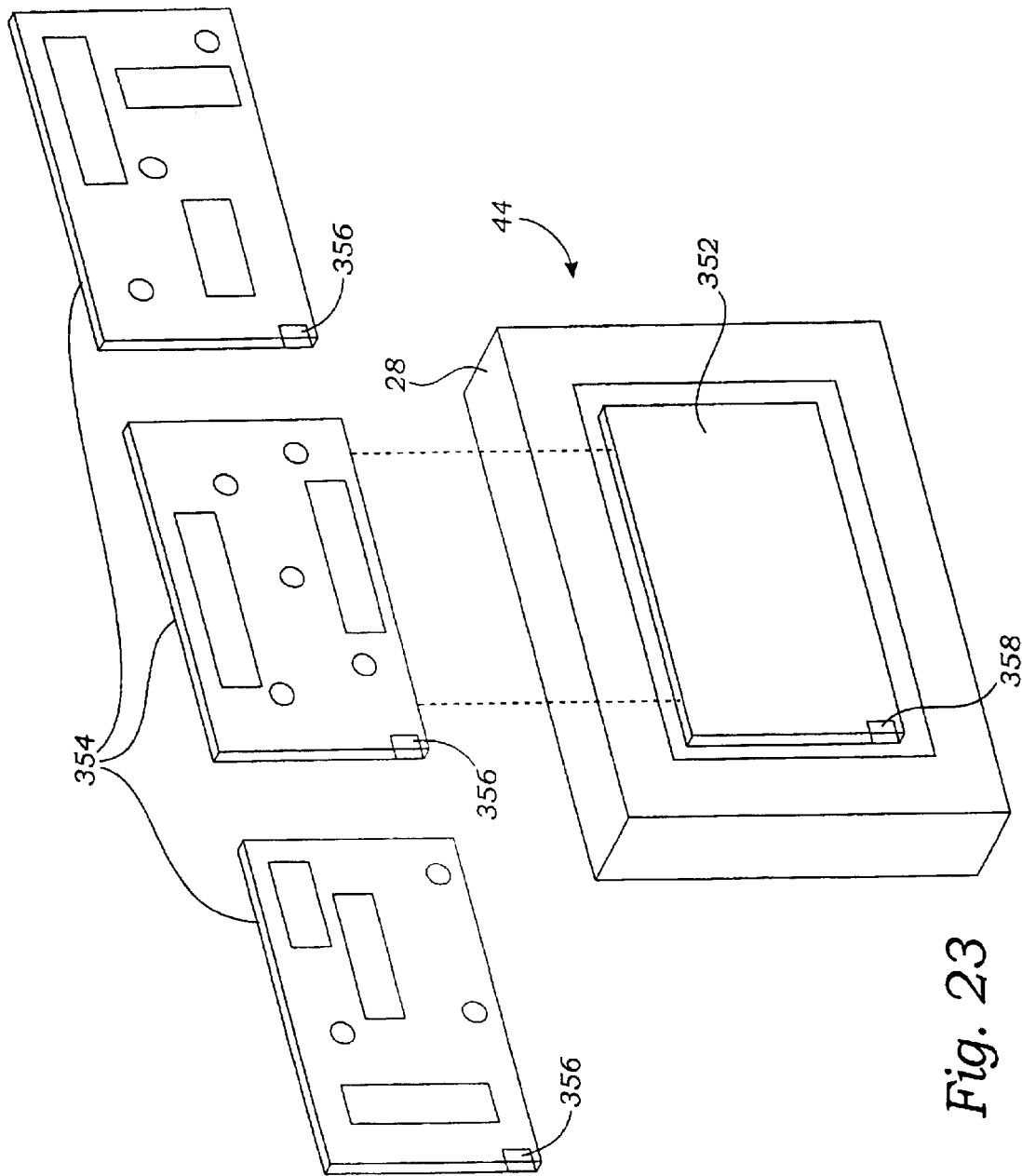
FIG. 23 is a perspective view of a generic user interface which can be customized by use of a family of interface templates, which the hemofiltration machine shown in FIG. 2 can incorporate.

As FIG. 23 shows, the interface 44 can include a generic display panel 352 that receives a family of templates 354. Each template 354 contains code 356 or chip that, when scanned or discerned by a reader 358 on the interface panel 352, programs the look and feel of the interface 44. In this way, a generic display panel 352 can serve to support a host of different interfaces, each optimized for a particular treatment modality.

Various features of the invention are set forth in the following claims.

We claim:

1. A fluid circuit assembly comprising flexible sheets sealed to form first and second panel sections, a pattern of seals formed in the first panel section to define a first fluid circuit, and a pattern of seals formed in the second panel section to define a second fluid circuit, the flexible sheets mutually aligned to place the first and second panel sections in a relationship with the first fluid circuit overlaying the second fluid circuit.

2. A fluid circuit assembly comprising first and second sheets of flexible material sealed to form first and second panel sections, a pattern of seals formed in the first panel section to define a first fluid circuit, and a pattern of seals formed in the second panel section to define a second fluid circuit, the flexible sheets being folded over to place the first and second panel sections in a reverse facing relationship with the first fluid circuit overlaying the second fluid circuit.

3. An assembly according to claim 1 or 2 wherein at least one of the first fluid circuit and the second fluid circuit includes an in-line clamping region that closes in response to an exterior force to occlude fluid flow in the first fluid circuit.

4. An assembly according to claim 1 or 2 wherein the first fluid circuit includes a first in-line clamping region that closes in response to an exterior force to occlude fluid flow in the first fluid circuit, wherein the second fluid circuit includes a second in-line clamping region that closes in response to an exterior force to occlude fluid flow in the second fluid circuit, and wherein the first in-line clamping region overlays the second in-line clamping region so that the first and second in-line clamping regions jointly close in response to an exterior force to occlude fluid flow in both the first and second fluid circuits.

5. An assembly according to claim 1 or 2 wherein at least one of the first fluid circuit and the second fluid circuit includes an in-line pump tube.

6. An assembly according to claim 1 or 2 wherein at least one of the first fluid circuit and the second fluid circuit includes an in-line sensor region to transmit pressure to an exterior pressure sensor.

7. An assembly according to claim 1 or 2 wherein at least one of the first fluid circuit and the second fluid circuit includes an in-line fluid holding compartment.

8. An assembly according to claim 1 or 2 wherein the first fluid circuit includes a first in-line fluid holding compartment, wherein the second fluid circuit includes a second in-line fluid holding compartment, and wherein the first in-line fluid holding compartment overlays the second in-line fluid holding compartment to mutually form a two-compartment chamber.

9. An assembly according to claim 1 or 2 further including at least one length of flexible tubing extending from a panel section and joined in fluid communication with the first fluid circuit or the second fluid circuit.

10. A fluid processing module comprising
a tray including walls defining an interior space, and
a fluid circuit assembly carried within the interior space comprising flexible material sealed to form first and second panels, a pattern of seals formed in the first panel to define a first fluid circuit, and a pattern of seals formed in the second panel to define a second fluid circuit, the flexible sheets being aligned within the interior space to place the first and second panels in a relationship with the first fluid circuit overlaying the second fluid circuit.

11. A fluid processing module comprising
a tray including walls defining an interior space, and
a fluid circuit assembly carried within the interior space comprising first and second sheets of flexible material sealed to form first and second panels, a pattern of seals formed in the first panel to define a first fluid circuit, and a pattern of seals formed in the second panel to define a second fluid circuit, the flexible sheets being folded over to place the first and second panels in a reverse facing relationship within the interior space, with the first fluid circuit overlaying the second fluid circuit.

12. A module according to claim 10 or 11
wherein at least one of the first fluid circuit and the second fluid circuit includes an in-line clamping region that closes in response to an exterior force to occlude fluid flow in the first fluid circuit, and
wherein a tray wall includes a cut-out to expose the in-line clamping region.

13. A module according to claim 10 or 11
wherein the first fluid circuit includes a first in-line clamping region that closes in response to an exterior force to occlude fluid flow in the first fluid circuit,
wherein the second fluid circuit includes a second in-line clamping region that closes in response to an exterior force to occlude fluid flow in the second fluid circuit,
wherein the first in-line clamping region overlays the second in-line clamping region so that the first and second in-line clamping regions jointly close in response to an exterior force to occlude fluid flow in both the first and second fluid circuits, and
wherein a tray wall includes a cut-out to expose the overlaying first and second in-line clamping regions.

14. A module according to claim 10 or 11
wherein at least one of the first fluid circuit and the second fluid circuit includes an in-line pump tube, and
wherein a tray wall includes a cut-out to expose the in-line pump tube.

15. A module according to claim 10 or 11
wherein at least one of the first fluid circuit and the second fluid circuit includes an in-line sensor region to transmit pressure to an exterior pressure sensor, and
wherein a tray wall includes a cut-out to expose the in-line sensor region.

16. A module according to claim 10 or 11
wherein at least one of the first fluid circuit and the second fluid circuit includes an in-line fluid holding compartment, and
wherein a tray wall includes a cut-out to expose the in-line fluid holding compartment.

17. A module according to claim 10 or 11
wherein the first fluid circuit includes a first in-line fluid holding compartment,
wherein the second fluid circuit includes a second in-line fluid holding compartment,
wherein the first in-line fluid holding compartment overlays the second in-line fluid holding compartment to mutually form a two-compartment chamber, and
wherein the tray includes a cut-out to expose the two-compartment chamber.

18. A module according to claim 10 or 11
further including at least one length of flexible tubing held in the interior space and joined in fluid communication with either the first fluid circuit or the second fluid circuit.

19. A fluid circuit for volumetrically balancing fluid comprising first and second sheets of flexible material sealed to form first and second panels, a pattern of seals formed in the first panel to define a first fluid circuit for handling out going fluid and including a first in-line compartment to retain a volume of out going fluid, and a pattern of seals formed in the second panel to define a second fluid circuit for handing in going fluid and including a second in-line compartment to retain a volume of in going fluid, the flexible sheets being aligned to place the first and second panels in a relationship with the first in-line compartment overlaying the second in-line compartment to mutually form a two-compartment chamber that displaces out going fluid from the first in-line compartment as in going fluid is conveyed into the second in-line compartment, and vice versa.

20. A fluid circuit according to claim 19
wherein the second fluid circuit includes a second in-line clamping region communicating with the second in-line compartment, the second in-line clamping region closing in response to an exterior force to occlude fluid flow.

21. A fluid circuit according to claim 20
wherein at least one of the first fluid circuit and the second fluid circuit includes an in-line pump tube.

22. A fluid circuit according to claim 20
wherein at least one of the first fluid circuit and the second fluid circuit includes an in-line sensor region to transmit pressure to an exterior pressure sensor.

23. A fluid circuit according to claim 19
wherein the first fluid circuit includes a first in-line clamping region communicating with the first in-line compartment, the first in-line clamping region closing in response to an exterior force to occlude fluid flow.

24. A fluid circuit according to claim 20
wherein the first fluid circuit includes a first in-line clamping region communicating with the first in-line compartment, the first in-line clamping region closing in response to an exterior force to occlude fluid flow,
wherein the first in-line clamping region overlays the second in-line clamping region so that the first and second in-line clamping regions jointly close in response to an exterior force to occlude fluid flow.

25. A flow management system, comprising:

first and second sheets of material sealed to form first and second panels, the first panel having a first fluid pathway for handling a first fluid comprising a first compartment to receive a volume of the first fluid, the second panel having a second fluid pathway for handling a second fluid comprising a second compartment to receive a volume of the second fluid, the panels being aligned so that the first compartment overlays the second compartment to form a structure so that the first fluid from the first compartment is displaced as the second fluid fills the second compartment.

26. The flow management system of claim 25, wherein the panels are aligned by folding.

27. The flow management system of claim 25, wherein the panels are die cut and overlay one another.

28. The flow management system of claim 25, wherein the sheets are flexible.

29. The flow management system of claim 25, wherein each panel has a pattern of seals.

30. The flow management system of claim 25, wherein the first fluid is an outgoing fluid.

31. The flow management system of claim 25, wherein the second fluid is an in-going fluid.

32. A flow management system, comprising a first panel having a first fluid pathway for handling a first fluid, the first panel comprising a first compartment to receive a volume of the first fluid and a second compartment to receive a volume of the first fluid; and a second panel having a second fluid pathway for handling a second fluid, the second panel comprising a third compartment to receive a volume of the second fluid and a fourth compartment to receive a volume of the second fluid, the panels being aligned so that the first compartment overlays the third compartment to form a structure so that the first fluid from the first compartment is displaced as the second fluid fills the third compartment, and the second compartment overlays the fourth compartment to form a structure so that the second fluid from the fourth compartment is displaced as the first fluid fills the second compartment.

33. The flow management system of claim 32, wherein the panels are aligned by folding.

34. The flow management system of claim 32, wherein the panels are die cut and overlay one another.

35. The flow management system of claim 32, wherein the panels are flexible.

36. The flow management system of claim 32, wherein each panel has a pattern of seals.

37. The flow management system of claim 32, wherein the first fluid is an outgoing fluid.

38. The flow management system of claim 32, wherein the second fluid is an in-going fluid.

39. A fluid circuit assembly comprising:

flexible sheets each arranged parallel and sealed to at least another to form first and second panels;

a pattern of seals formed in the first panel section to define a first fluid circuit;

a pattern of seals formed in the second panel section to define a second fluid circuit;

the first and second panels mutually alignable to place the first and second panels in such a relationship that the first fluid circuit overlies the second fluid circuit.

40. A fluid circuit assembly comprising:

flexible sheets sealed to form first and second panel sections;

a pattern of seals formed in the first panel section to define a first fluid circuit portion;

a pattern of seals formed in the second panel section to define a second fluid circuit portion;

the panel sections being aligned to place at least part of the first and second fluid circuit portions in an overlying relationship such that two layers of said sheets separate said parts of said first and second fluid circuit portions, each layer corresponding to a respective one of said first and second fluid circuits, whereby a force of an actuator may be applied through said two layers.

41. A fluid circuit for volumetrically balancing fluid comprising first and second sheets of flexible material sealed to form first and second panels, a pattern of seals formed in the first panel to define a first fluid circuit for handling out going fluid and including a first in-line compartment to retain a volume of out going fluid, and a pattern of seals formed in the second panel to define a second fluid circuit for handing in going fluid and including a second in-line compartment to retain a volume of in going fluid, the flexible sheets being aligned to place the first and second panels in a relationship with the first in-line compartment overlaying the second in-line compartment to mutually form a two-compartment chamber, such that the first and second in-line compartments are divided by two layers formed by said sheets, each corresponding to a respective one of said first and second in-line compartments, the two-compartment chamber displaces out going fluid from the first in-line compartment as in going fluid is conveyed into the second in-line compartment, and vice versa.

* * * * *